US007014842B2

(12) United States Patent
Dueva-Koganov et al.

(10) Patent No.: US 7,014,842 B2
(45) Date of Patent: Mar. 21, 2006

(54) SUNSCREEN COMPOSITION

(75) Inventors: Olga V. Dueva-Koganov, White Plains, NY (US); James P. SaNogueira, Suffern, NY (US)

(73) Assignee: Playtex Products, Inc., Westport, CT (US)

(*) Notice: Subject to any disclaimer, the term of this patent is extended or adjusted under 35 U.S.C. 154(b) by 78 days.

(21) Appl. No.: 10/856,737

(22) Filed: May 28, 2004

(65) Prior Publication Data

US 2005/0013781 A1 Jan. 20, 2005

Related U.S. Application Data

(60) Provisional application No. 60/474,362, filed on May 29, 2003.

(51) Int. Cl.
A61K 7/42 (2006.01)
A61K 7/44 (2006.01)
A61K 7/00 (2006.01)

(52) U.S. Cl. ............... 424/59; 424/60; 424/400; 424/401

(58) Field of Classification Search ............ 424/59, 424/60, 400, 401
See application file for complete search history.

(56) References Cited

U.S. PATENT DOCUMENTS

| | | | |
|---|---|---|---|
| 4,422,952 A | 12/1983 | Koulbanis et al. | |
| 4,869,897 A | 9/1989 | Chatterjee et al. | |
| 4,954,332 A | 9/1990 | Bissett et al. | |
| 5,505,935 A | 4/1996 | Guerro et al. | |
| 5,576,354 A | 11/1996 | Deflandre et al. | 514/685 |
| 5,599,533 A | 2/1997 | Stepniewski et al. | |
| 5,693,329 A | 12/1997 | Marchi-Lemann et al. | |
| 5,783,173 A | 7/1998 | Bonda et al. | |
| 5,788,954 A | 8/1998 | Bonda et al. | |
| 5,833,961 A | 11/1998 | Siegfried et al. | |
| 5,849,273 A | 12/1998 | Bonda et al. | |
| 5,993,789 A | 11/1999 | Bonda et al. | |
| 6,024,942 A | 2/2000 | Tanner et al. | |
| 6,033,649 A | 3/2000 | Gonzenbach et al. | 424/60 |
| 6,051,211 A | 4/2000 | Hansenne et al. | |
| 6,113,931 A | 9/2000 | Bonda et al. | |
| 6,123,927 A | 9/2000 | Ogawa et al. | |
| 6,126,925 A | 10/2000 | Bonda et al. | |
| 6,129,909 A | 10/2000 | Bonda et al. | |
| 6,180,091 B1 | 1/2001 | Bonda et al. | |
| 6,210,658 B1 | 4/2001 | Bonda et al. | |
| RE37,198 E | 5/2001 | Ser et al. | |
| 6,274,124 B1 | 8/2001 | Vollhardt | |
| 6,284,916 B1 | 9/2001 | Bonda et al. | |
| 6,290,938 B1 | 9/2001 | Tanner et al. | |
| 6,328,987 B1 | 12/2001 | Marini | |
| 6,350,894 B1 | 2/2002 | Bonda et al. | |
| 6,355,261 B1 | 3/2002 | Bonda et al. | |
| 6,384,104 B1 | 5/2002 | Chang et al. | |
| 6,440,402 B1 | 8/2002 | Gonzalez et al. | |
| 6,444,195 B1 | 9/2002 | Cole et al. | |
| 6,461,622 B1 | 10/2002 | Liu et al. | |
| 6,485,713 B1 | 11/2002 | Bonda et al. | 424/59 |
| 6,518,451 B1 | 2/2003 | Bonda et al. | |
| 6,521,217 B1 | 2/2003 | Luther et al. | |
| 6,537,529 B1 | 3/2003 | Bonda | |
| 6,551,605 B1 | 4/2003 | Bonda et al. | |
| 6,607,713 B1 | 8/2003 | Chodorowski et al. | |
| 6,770,270 B1 | 8/2004 | Bonda et al. | |
| 6,800,274 B1 | 10/2004 | Bonda et al. | |
| 2002/0155072 A1 | 10/2002 | Knuppel et al. | |
| 2003/0180232 A1 | 9/2003 | Ishii et al. | |
| 2004/0047817 A1 | 3/2004 | Bonda et al. | |
| 2004/0047818 A1 | 3/2004 | Bonda | |
| 2004/0057913 A1 | 3/2004 | Bonda et al. | |
| 2004/0166072 A1 | 8/2004 | Bonda | |
| 2004/0185016 A1 | 9/2004 | Popp et al. | |

FOREIGN PATENT DOCUMENTS

| | | |
|---|---|---|
| EP | 848944 | 6/1998 |
| EP | 930063 | 7/1999 |
| WO | WO 3075877 | 9/2003 |

OTHER PUBLICATIONS

Article: "A Method for Broad Spectrum Classification of Sunscreen" By B.L. Diffey, International Journal of Cosmetic Science 16, pp. 47-52 1994.
Article: "FDA Final Monograph for Sunscreen Testing," by Department of Health and Human Services, Federal Register/vol. 64, No. 98/ May 21, 1999/Rules and Regulations pp. 27666-27693.
International Search Report corresponding to PCT International Application No. PCT/USO4/17037 Apr. 1, 2005.

*Primary Examiner*—Shelley A. Dodson
(74) *Attorney, Agent, or Firm*—Ohlandt, Greeley, Ruggiero & Perle, L.L.P.

(57) ABSTRACT

There is provided a composition comprising one or more photoactive compounds and one or more optimization agents. Surprisingly, the composition requires a small amount of optimization agent to efficiently optimize the polarity, critical wavelength, SPF, PFA, Star Rating, photostability, or any combinations thereof, of the composition. Subsequently, an efficient sunscreen composition is achieved.

94 Claims, 7 Drawing Sheets

SUNSCREEN COMPOSITION

RELATED APPLICATION

This application claims priority to pending U.S. Provisional Patent Application Ser. No. 60/474,362 filed on May 29, 2003, which is incorporated in its entirety by reference herein.

BACKGROUND OF THE INVENTION

1. Field of the Invention

The present invention relates generally to a photoprotective composition. More particularly, the present invention relates to a sunscreen composition having optimized polarity, critical wavelength, SPF PFA, photostability, Star Rating, or any combinations thereof. The present invention also relates generally to a method of optimizing photoprotective compositions.

2. Description of the Prior Art

Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays.

Typically, the above-described UV-B filters are combined with the above-described UV-A filters in a solution with other lipophilic or oily ingredients and solvents to form an oil phase. The solvents are used to dissolve the sunscreen actives into the oil phase. Typically, but not necessarily, the oil phase is dispersed with the help of emulsifiers and stabilizers into an aqueous solution composed primarily of water, to make an emulsion, which becomes the final sunscreen composition.

One problem associated with the use of UV filters, and especially those that are rapidly-degrading photoactive compounds, is that they are not photostable and will degrade rapidly and exponentially when exposed to UV radiation. The organic UV-A filters most commonly used in commercial sunscreen compositions are the dibenzoylmethane derivatives, particularly 4-(1,1-dimethylethyl)-4'-methoxy-dibenzoylmethane (also called avobenzone, sold under the brand name PARSOL 1789). Other dibenzoylmethane derivatives described as UV-A filters are disclosed in U.S. Pat. Nos. 4,489,057; 4,387,089 and 4,562,067, the disclosures of which are hereby incorporated herein by reference. It is also well known that the above described UV-A filters, particularly the dibenzoylmethane derivatives, can suffer in rapid photochemical degradation, when used alone or when combined with the above-described most commercially used UV-B filters. Thus, the efficiency of the sunscreen composition (i.e., SPF, PFA, critical wavelength, Star Rating) containing these photoactive compounds is compromised, unless the photodegradation is controlled by improving the photostability of the system in UVA and/or UVB regions.

By controlling the polarity of the solvent used in a sunscreen composition, the rate of photodecay of the photoactive compounds in the composition can be controlled. By controlling the polarity, greater stability is imparted to the photoactive compounds, thus resulting in a more stable overall composition. The dielectric constant, for example, is a good indicator or measure of polarity in a composition. This is due to the fact that the dielectric constant is a measure of both inherent and inducible dipole moments.

In addition, polar solvents tend to decrease the energy required to excite a pi-bonding electron, and increase the energy required to excite a non-bonding electron. This phenomenon is called "state switching" and is a mechanism by which photoactive compounds absorb UV radiation. By enhancing the state switching in a photoprotective or sunscreen composition, a more efficient UV absorbing composition can result.

It is also known that the use of different solvents in sunscreen formulations may increase or decrease the effectiveness of a sunscreen chemical. The shifts (hypsochromic to the lower wavelength or bathochromic to higher wavelength) in the UV spectrum are due to the relative degrees of solvation by the solvent of the ground state and the excited state of the chemical.

It has been found in the prior art that as the polarity of a solvent system including a dissolved, rapidly-photodegradable compound is increased, the rate of photodecay initially decreases, but then increases again as the polarity is further increased. Thus, a photodegradable compound in solution will degrade as a second-order function of the overall polarity of the solution. Currently accepted photochemical theory provides the possibility that the mechanism by which a photodegradable compound is stabilized is the transfer of a photonically-excited electron to a nearby molecule of the same or different species (see, e.g., N. J. Turro, Modem Molecular Photochemistry, Chapter 9, Benjamin/Cummings Publ. Co., Menlo Park, Calif. (1991)), incorporated by reference herein. Additional photochemical theory is believed to coincide with the electron transfer theory of Professor Rudolph A. Marcus of the California Institute of Technology, for which he received the 1992 Nobel Prize in Chemistry, incorporated by reference herein.

U.S. Pat. Nos. 6,485,713 and 6,537,529 to Bonda et al., consistent with the above-described theory, discloses the use of amides, malates and bis-urethanes in a solvent system to control the polarity of the solvent system in a sunscreen composition. The use of these specific components results in an oil phase having a dielectric constant no greater than about 12. The named components are used in an oil-in-water sunscreen composition in an amount about 0.1% to about 40% by weight of the total weight of the composition, and more preferably about 3 wt. % to about 20 wt. %.

In addition to the above, U.S. Patent Application Publication No. 2004/0057916 A1 to Bonda et al. discloses polymers and compounds including a diphenylmethylene or a 9H-fluorene moiety for use in sunscreen compositions to photostabilize UVA sunscreen actives.

Critical wavelength is another important aspect in optimizing the performance of a photoprotective composition. In 1994, Diffey described the Critical Wavelength in vitro method, which is based on the absorption spectrum of a sunscreen product obtained via UV substrate spectrophotometry (Diffey B L (1994) A Method for Broad-Spectrum Classification of Sunscreens. Intl J Cosmet Sci, 16: 47–52), which is incorporated by reference herein. The absorption spectrum of a sunscreen is characterized by an index, namely critical wavelength, which is the wavelength where the integral of the spectral absorbance curve reached 90% of the integral from 290 nm to 400 nm. The critical wavelength method is used to determine the breadth of UV protection and is the recommended method for the evaluation of long wave efficacy of sunscreen products. Therefore, by optimizing the critical wavelength properties of a photoprotective composition, enhanced photoprotection may result.

Another measure of a sunscreen composition's efficiency is the Star Rating (UVA/UVB Ratio) according to the Boots Star Rating System (4-star that was recently revised to 5 star category). The Star Rating is calculated as an indicator of the UVA absorbance properties of a sunscreen product, relative to UVB as described in the Revised Guidelines to the practical measurement of UVA:UVB ratios according to Boots Star Rating System. The calculation of the UVA:UVB absorbance ratio will typically yield values from zero (equal to no UVA absorbance) up to 1.0 (UVA absorbance equal to UVB).

What is absent in the prior art is a photoprotective composition having one or more agents that differ from the prior art that are capable of optimizing at least one of the following properties: polarity, critical wavelength, SPF, PFA, Star Rating, or any combinations thereof, in the oil phase, water phase, both phases, or the final sunscreen formulation; thus resulting in a more efficient and photostable photoprotective composition.

The present invention addresses this shortcoming by providing an efficient photoprotective composition having one or more optimization agents capable of optimizing at least one of the following properties: polarity, critical wavelength, SPF, PFA, Star Rating, photostability or any combinations thereof, in the oil phase, water phase, both phases of the composition, or the final sunscreen formulation.

SUMMARY OF THE INVENTION

It is an object of the present invention to provide an efficient photoprotective composition.

It is another object of the present invention to provide such a composition that is a sunscreen composition.

It is still another object of the present invention to provide such a composition having one or more optimization agents capable of optimizing the polarity, critical wavelength, SPF, PFA, Star Rating, photostability, or any combinations thereof of the oil phase, water phase, both oil and water phases, of the composition.

It is another object of the present invention to provide such a composition where the one or more optimization agents are lipophilic, hydrophilic, or both.

It is still another object of the present invention to provide such a composition where the one or more optimization agents have a dielectric constant greater than about 10.5.

It is still another object of the present invention to provide such a composition where the one or more optimization agents have a dielectric constant greater than about 13.

It is a further object of the present invention to provide such a composition where the one or more optimization agents are one or more alcohols, such as, for example, glycols, diols, or any derivatives thereof.

These and other objects of the present invention are achieved by a composition comprising one or more photoactive compounds and one or more optimization agents.

Surprisingly, the composition requires a small amount of optimization agent to efficiently optimize the polarity, critical wavelength, SPF, PFA, Star Rating, photostability, or any combinations thereof, of the composition. Subsequently, an efficient sunscreen composition is achieved.

DETAILED DESCRIPTION OF THE INVENTION

Figure 1:
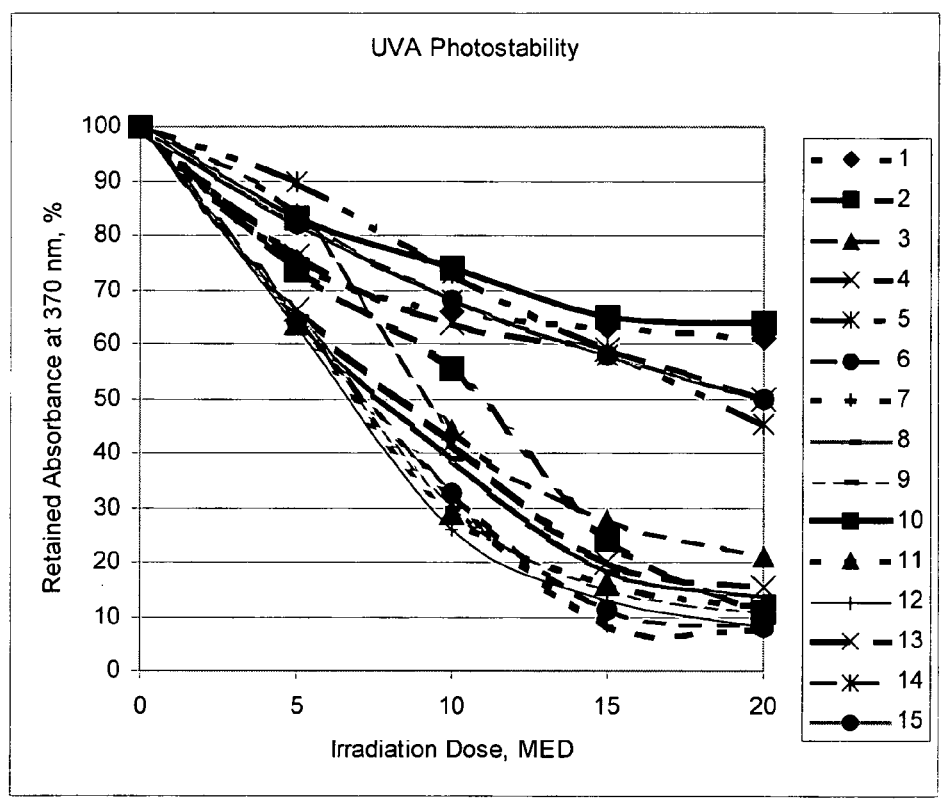
FIG. 1 is a graph depicting the UVA photostability of compositions according to the present invention and comparative examples.

The present invention provides photoprotective compositions that are uniquely formulated with one or more optimization agents that results in the optimization of one or more of the following properties: polarity, critical wavelength, SPF, PFA, Star Rating (UVA/UVB Ratio), photostability, or any combinations thereof, of the composition. Photoprotective compositions according to the present invention include, but are not limited to, sunscreens, cosmetics, paints, coatings, and the like.

A photoactive compound, as used herein, is a compound that responds to UV radiation photoelectrically. Examples of photoactive compounds include, but are not limited to, UV filters, pigments, or dyes.

By way of example, the present invention is illustrated herein by reference to a sunscreen composition for use on mammalian hair and/or skin. It is to be understood, however, that the principles set forth below apply equally to any photoprotective composition.

According to the present invention, a sunscreen composition is provided having one or more photoactive agents and one or more optimization agents. The resulting sunscreen composition is photostable and possesses optimized polarity, critical wavelength, SPF, PFA, Star Rating, photostability, or any combinations thereof, which results in a more efficient UV radiation-absorbing composition.

The one or more photoactive agents suitable for use in the sunscreen composition of the present invention include one or more UV filters. Suitable UV filters may include, but are not limited to, one or more compounds selected from the following categories (with specific examples): p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naptholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone), dibenzoylmethane derivatives, avobenzone, 4-isopropyldibenzoylmethane, butylmethoxydibenzoylmethane, 4-isopropyl-dibenzoylmethane, octocrylene, drometrizole trisiloxane, and metal oxides (titanium dioxide, zinc oxide).

In one embodiment of the invention a photoactive compound is selected from the group consisting of UV-A filters, UV-B filters, or any combinations thereof. In a cosmetically-acceptable sunscreen embodiment for use on human skin, a photoactive compound preferably is selected from approved (if regulated), cosmetically-acceptable UV-A filters, UV-B filters, or any combinations thereof.

For example, for a product marketed in the United States, preferred cosmetically-acceptable photoactive compounds and concentrations (by way of example, reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3 diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and concentrations (by way of example, percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and concentrations (by way of example, reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine.(10% or less, also called TINOSORB S), Mexoryl XL (also called drometrizole trisiloxane, 15% or less), Mexoryl SX (15% or less).

The one or more photoactive compounds are present in the composition in an amount about 1% to about 40% by weight of the total weight of the sunscreen composition. The amount of sunscreen agent in the composition can vary in the above range depending on the sun protection factor (SPF) desired. Usually, the higher the SPF, the greater the total amount of sunscreen agent used in the composition. However, as demonstrated herein, the present invention provides the possibility of formulating a photoprotective composition with an increased or boosted SPF without the inclusion of additional sunscreen agent or increasing the total amount of sunscreen agent in the composition.

Preferably, the one or more sunscreen agents are included at about 2 wt. % to about 35 wt. % to achieve a SPF of about 2 to about 50. More preferably, the one or more sunscreen agents are included in an amount about 4 wt. % to about 30 wt. % to achieve a SPF value of about 4 to about 45.

The composition of the present invention must include one or more optimization agents. It has been unexpectedly found that the inclusion of one or more optimization agents according to the present invention in a sunscreen composition results in a stable, efficient composition.

The one or more optimization agents may be present in a photoprotective composition according to the present invention from about 0.1 wt. % to about 40 wt. %, based on the total weight of the composition. Preferably, the one or more optimization agents are present from about 0.5 wt. % to about 15 wt. %, and more preferably from about 1 wt. % to about 11 wt. %, based on the total weight of the composition.

Surprisingly, it has been found that only small amounts of the one or more optimization agents, on the order of about 0.1 wt. % to about 10 wt. %, based on the total weight of the composition, are required to effect the desired optimization of polarity, critical wavelength, SPF, PFA, Star Rating (UVA/UVB Ratio), photostability, or any combinations thereof, in the composition. Preferably, the one or more optimization agents, taken alone or in combination, have a dielectric constant greater than about 10.5. More preferably, the one or more optimization agents, taken alone or in combination, have a dielectric constant greater than about 13.

Suitable optimization agents for use in the present invention may include, but are not limited to, diols, alcohols, glycols, polyhydric alcohols, polyhydric alcohol derivatives having one or more hydroxyl groups, or any combinations thereof. Preferably, the one or more optimization agents are one or more alcohols. More preferably, the one or more optimization agents are one or more diols, glycols, or any combinations thereof. Most preferably, diols are 1,2-diols.

Suitable glycols for use in the invention include, but are not limited to, pentylene glycol (1,2-pentanediol), neopentyl glycol (neopentanediol), caprylyl glycol (1,2-octanediol), etoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof. It is believed that glycols, such as those listed above, have a dielectric constant greater than about 10.5.

Determining the polarity of a mixture or an emulsion can be performed in various ways. For example, determining a polarity can include measuring a property that is a function of polarity, such as a dielectric constant. Measurement of a dielectric constant of a liquid can be performed by various sensors, such as immersion probes, flow-through probes, and cup-type probes, attached to various meters, such as those available from the Brookhaven Instruments Corporation of Holtsville, N.Y. (e.g., model BI-870) and the Scientifica Company of Princeton, N.J. (e.g. models 850 and 870). For consistency of comparison, preferably all measurements for a particular filter system are performed at substantially the same sample temperature, e.g., by use of a water bath. Generally, the measured dielectric constant of a substance will increase at lower temperatures and decrease at higher temperatures.

Dielectric Constants of the following glycols and their derivatives have been measured (see Table 1).

TABLE 1

Dielectric Constants

| Glycols/derivatives | Trade Name/ Manufacturer | Dielectric Constant, 23° C. |
|---|---|---|
| Pentylene Glycol | Hydrolite-5/Symrize | 18.2 |
| Diethylene Glycol Monobutyl Ether | ™ DB Solvent/ Eastman | 10.59 |
| 1,2-Hexanediol and 1,2-Octanediol (50:50 mixture) | Symdiol 68/Symrize | 13.07 |
| Ethoxydiglycol | Educol-421/MMP | 13.69 |
| Butylene Glycol Monopropionate | BG Monopropionate/ MMP | 11.72 |
| 1,2-Octanediol (Caprylyl Glycol) | LexGard O/Inolex | 10.61 (measured at 30° C.)* |
| 1,2-Hexanediol | | 15.1 |
| Polyethylene Glycol-7 Methyl Ether | Sasol | 13.1 |

*Solid at room temperature (23 C.).

It has been surprisingly found that the inclusion of one or more optimization agents in a composition according to the present invention results in a SPF boost on the order of at least 25% as compared to a composition without one or more optimization agents. Particularly, a SPF boost on the order of at least about 30% is experienced by a composition according to the present invention.

In order to evaluate the unexpected SPF boost in photoprotective compositions by the one or more optimization agents according to the present invention, by way of example, the performance of 1,2-octanediol (caprylyl glycol) and pentylene glycol in vivo was evaluated. The following formulations outlined in Table 2 were tested in SPF studies (static and Very Water Resistant (VWR)). The SPF was determined using the method outlined in the Food and Drug Administration (FDA) Final Monograph for sunscreen testing published in the Federal Register, Vol. 64, No. 98, May 21, 1999, which is incorporated by reference herein.

Referring to Table 2 below, the differences among the formulations are the presence or absence of 1,2-octanediol (caprylyl glycol) and/or octocrylene.

TABLE 2

Sunscreen Compositions

| Chemical/INCI/USP Name | Trade Name | MF2822-1 % w/w | MF2822-2 % w/w | MF2770-114 % w/w |
|---|---|---|---|---|
| Octinoxate | Neo Heliopan AV | 7.50 | 7.50 | 7.50 |
| Octyl Salicylate | Neo Heliopan OS | 5.00 | 5.00 | 5.00 |
| Homosalate | Escalol 567 | 5.00 | 5.00 | 5.00 |
| Avobenzone | Parsol 1789 | 3.00 | 3.00 | 3.00 |
| Octocrylene | | NONE | NONE | 2.50 |
| Purified Water | | 60.03 | 65.03 | 62.53 |
| Neopentyl Glycol Diheptanoate | Lexfeel 7 | 5.00 | 5.00 | 5.00 |
| 1,2-Octanediol | LexGard O | 5.00 | NONE | NONE |
| Tapioca Starch | Stabilex T | 2.50 | 2.50 | 2.50 |
| Acrylates/C12–22 Alkylmethacrylate Copolymer | Allianz OPT | 2.50 | 2.50 | 2.50 |
| Glycerin | Emery 917 | 2.00 | 2.00 | 2.00 |
| Phenoxyethanol (and) Methylparaben (and) Butylparaben (and) Ethylparaben (and) Propylparaben (and) Isopropylparaben | Phenonip | 1.00 | 1.00 | 1.00 |
| Triethanolamine | TEA 99% | 0.53 | 0.53 | 0.53 |
| PEG-20 Almond Glycerides | Crovol A-40 | 0.35 | 0.35 | 0.35 |
| Acrylates/C10–30 AlkylAcrylate Crosspolymer | Pemulen TR-2 | 0.27 | 0.27 | 0.27 |
| Carbomer | Ultrez 10 | 0.15 | 0.15 | 0.15 |
| Tocopheryl Acetate (USP) | Tocopheryl Acetate | 0.05 | 0.05 | 0.05 |

TABLE 2-continued

Sunscreen Compositions

| Chemical/INCI/USP Name | Trade Name | MF2822-1 % w/w | MF2822-2 % w/w | MF2770-114 % w/w |
|---|---|---|---|---|
| Disodium EDTA | Dissolvine Na2S | 0.07 | 0.07 | 0.07 |
| Aloe Barbadensis Leaf Extract | Aloe Oil Extract 101 | 0.05 | 0.05 | 0.05 |
| | | 100.00 | 100.00 | 100.00 |

The results of the SPF tests are outlined below in Tables 3 through 5.

TABLE 3

Results for MF2822-1

| | SPF Static | SPF VWR |
|---|---|---|
| Average SPF (N = 5) | 37.06 | 35.00 |
| Standard Deviation | 2.20 | 0.00 |
| Standard Error | 0.98 | 0.00 |
| t (one-tail) | 2.132 | 2.132 |
| A | 2.10 | 0.00 |
| SPF Label | 34.96 | 35.00 |

TABLE 4

Results for MF2822-2

| | SPF Static | SPF VWR |
|---|---|---|
| Average SPF (N = 5) | 28.38 | 28.38 |
| Standard Deviation | 1.65 | 1.65 |
| Standard Error | 0.74 | 0.74 |
| t (one-tail) | 2.132 | 2.132 |
| A | 1.57 | 1.57 |
| SPF Label | 26.81 | 26.81 |

TABLE 5

Results for MF2770-114

| | SPF Static | SPF VWR |
|---|---|---|
| Average SPF (N = 21) | 37.02 | 36.25 |
| Standard Deviation | 2.98 | 2.29 |
| Standard Error | 0.65 | 0.50 |
| t (one-tail) | 1.725 | 1.725 |
| A | 1.12 | 0.86 |
| SPF Label | 35.00 | 35.00 |

The results of SPF tests demonstrate that the addition of 5 wt. % of 1,2-octanediol (caprylyl glycol) to the sunscreen formulation provided an SPF boost of more than 8 SPF units (about 30.5%) when compared to the formulation without 1,2-octanediol (caprylyl glycol). Sunscreen formulation with 5 wt. % of 1,2-octanediol (caprylyl glycol) and without octocrylene has a SPF VWR of 35.0, which is the same as the formulation with 2.5 wt. % of octocrylene and without 1,2-octanediol. Overall, the inclusion of one or more optimization agents according to the present invention, such as, for example, 1,2-octanediol (caprylyl glycol), in a sunscreen formulation results in a significant SPF boost. In addition, the inclusion of one or more optimization agents in a sunscreen formulation can result in a composition having a desired SPF with less amount of sunscreen active in the composition.

EXAMPLE 2

The following additional example demonstrates the effectiveness of the present invention in providing a stable and efficient photoprotective composition. A comparison of a composition according to the present invention (Comp. B) having a optimizing agent (in this case pentylene glycol) to one not having an optimization agent (Comp. A) is set forth below. The test methodology used to determine SPF is the same as that described above with respect to Example 1.

TABLE 6

Sunscreen Compositions With and Without Pentylene Glycol

| | Weight % | |
|---|---|---|
| INCI Adopted Name | Comp. A | Comp. B |
| Water | 62.3773 | 60.8773 |
| Octyl Methoxycinnamate | 7.5000 | 7.5000 |
| Ethylhexyl Salicylate | 5.0000 | 5.0000 |
| C12–15 Alkyl Benzoate | 5.0000 | 5.0000 |
| Benzophenone-3 | 4.1000 | 4.1000 |
| Isopropyl Myristate | 4.0000 | 4.0000 |
| Cocoglycerides | 3.5000 | 3.5000 |
| Glycerin | 2.0000 | 2.0000 |
| Acrylates/C12–22 Alkylmethylacrylate Copolymer | 2.0000 | 2.0000 |
| Butyl methoxydibenzoylmethane | 1.5000 | 1.5000 |
| Pentylene Glycol | NONE | 1.5000 |
| Phenoxyethanol (and) Methylparaben (and) Butylparaben (and) Ethylparaben (and) Propylparaben (and) Isobutylparaben | 1.0000 | 1.0000 |
| Triethanolamine | 0.6500 | 0.6500 |
| PEG-20 Almond Glycerides | 0.3500 | 0.3500 |
| Acrylates C10–30 Alkyl Acrylate Crosspolymer | 0.3000 | 0.3000 |
| Fragrance | 0.2000 | 0.2000 |
| Carbomer | 0.1500 | 0.1500 |
| Xanthan Gum | 0.1000 | 0.1000 |
| Disodium EDTA | 0.0700 | 0.0700 |
| Tocopheryl Acetate | 0.0500 | 0.0500 |
| Aloe Barbadensis Leaf Extract | 0.0500 | 0.0500 |
| Carthamus Tinctorius (Safflower) Seed Oil (and) Chamomile Recutita (Matricaria) Extract | 0.0500 | 0.0500 |
| Carthamus Tinctorius (Safflower) Seed Oil (and) Lavandula Angustifolia (Lavender) Extract | 0.0500 | 0.0500 |
| Yellow 5 | 0.0020 | 0.0020 |
| Green 5 | 0.0007 | 0.0007 |
| TOTAL: | 100.0000 | 100.0000 |
| Average SPF Static in vivo | <25.68 | 31.76 |
| Average SPF VWR in vivo | <24.12 | 31.22 |

As is evident from this example, the inclusion of optimization agent according to the present invention, such as 1.5 wt. % pentylene glycol (1,2-pentanediol) in the sunscreen formulation (Comp. B), results in an increase in SPF by more that 6 units (about 29%) due to the increased polarity of the oil phase.

While, as noted above, it has been unexpectedly found that one or more optimization agents according to the present invention boost SPF, it has also been unexpectedly found that the one or more optimization agents also photostabilize UVA sunscreens, such as avobenzone and its derivatives, and UVB sunscreens. As a result, both UVA and UVB protection is optimized. This is demonstrated by way of Example 3 below.

EXAMPLE 3

Test compositions were prepared with octocrylene (Positive control), glycols, glycol derivatives, or isopropyl myristate (Negative control) added to the following sunscreen components: AVOBENZONE—3 g; HOMOSALATE—15 g; OCTYL SALICYLATE—5 g, thus imitating the oil phase of a sunscreen formulation (see Table 7):

TABLE 7

Compositions

| # | ADDITIVE: | g | DEC, 23 C. |
|---|---|---|---|
| Positive Control 1 | Octocrylene | 5 | 7.89 |
| 2 | Pentylene Glycol | 5 | 10.5 |
| 3 | Ethoxydiglycol (Diethylene glycol monoethyl ether) | 5 | 8.59 |
| 4 | BG Monopropionate | 5 | 8 |
| 5 | 1,2-Octanediol (Caprylyl Glycol) | 5 | 8.1 |
| Negative Control 6 | Isopropyl Myristate | 5 | 6.15 |
| 7 | 1,2-Hexanediol + 1,2-Octanediol | 5 | 7.8 |
| 8 | Diethylene Glycol Monobutyl Ether | 5 | 7.6 |
| 9 | 1,2-Hexanediol | 5 | 8 |
| 10 | Octocrylene + 1,2-Octanediol | 2.5 + 2.5 | 7.8 |
| Negative Control 11 | No additives | 0 | 7.03 |
| 12 | PEG-7 Methyl Ether | 5 | 7.69 |
| 13 | Octocrylene | 2.5 | 7.79 |
| 14 | Octocrylene and PEG-7 Methyl Ether | 2.5 + 2.5 | 8.36 |
| 15 | Octocrylene + 1,2-Octanediol + PEG-7 Methyl Ether | 2.5 + 1.25 + 1.25 | 8.39 |

Referring to Table 7 above, the compositions were applied on Vitro-Skin (0.6 mg/cm2) and irradiated. The irradiation dose was 5 MEDs repeated 4 times (=20 MEDs total). Retained Absorbance at 370 nm (UVA photostability, FIG. 1), 310 nm (UVB photostability, FIG. 2) and critical wavelength (Table 8, FIG. 3) were determined for each composition before and after each irradiation dose in order to determine their photostability.

For each sunscreen composition, the filter system was blended with the solvent system to form an oil phase. Next, the dielectric constant of the oil phase was measured. Dielectric constant measurements were performed with a Scientifica Model 850 dielectric constant meter.

The resulting sunscreen oil phases were tested for photostability by measuring absorbance on a Labsphere UV-1000S Ultraviolet Transmittance Analyzer before and after irradiation with a Solar Light Company model 16S solar simulator (equipped with a WG 320 filter to transmit radiation greater than 290 nm) in 5 MED (105 mJ/cm.sup.2) increments up to 20 MED cumulative dose. Output was monitored by a PMA 2105 UV-B DCS Detector (biologically weighted) and controlled by a PMA 2100 Automatic Dose Controller (Solar Light Co.).

A synthetic skin substrate was used for testing the sunscreen compositions (VITRO-SKIN substrate by IMS, Inc. of Milford, Conn.). To prepare the substrate, a 300 g solution of 44 g of glycerin and 256 g of deionized water was added to an IMS hydrating chamber, and a sheet of VITRO-SKIN was placed in the hydrating chamber for approx. 16 hours. Several 6.5 cm squares were cut from the hydrated VITRO-SKIN and used for absorbance measurements.

To prepare slides for testing, sunscreen composition is drawn or placed into a pipette. The test composition is uniformly applied to VITRO-SKIN square (0.6 mg/cm$^2$). This application dose of the oil phase, 0.6 mg/cm$^2$, corresponds to the application dose of 2 mg/cm$^2$ of sunscreen formulation (typically the concentration of the oil phase in the sunscreen formulation is about 30%). The VITRO-SKIN square was then placed on a foam block, and the test material was spread by finger (covered with a latex glove or finger cot), first in a circular motion, then by a side-to-side motion during which the VITRO-SKIN is deformed by the pressure. The square was then mounted in a slide holder and allowed to dry for about 15 to 20 minutes.

To test photostability, a slide was positioned on the UV transmittance analyzer using registration marks, and a scan of 1 sq. cm spot on the slide was performed. The slide was then transferred to a holder placed adjacent to the solar simulator and, using a calipers, was positioned such that the beam of UV radiation exiting the solar simulator illuminated the same 1 cm spot on the slide. The following software settings were used: UV-B—290–320 nm; UV-A—320–400 nm; SPF—290–400 nm; Spectral Irradiance; Noon, July 3, Albuquerque, N.Mex.; SPF Spectral Irradiance and Erythermal Effectiveness settings as set by manufacturer. Following an exposure of 5 MED, the slide was again placed in position on the UV transmittance analyzer, and a scan of the exposed spot was performed. The procedure was repeated on the same 1 cm spot on the slide until the desired total radiation dosage was achieved.

TABLE 8

Critical Wavelength

| Critical Wavelength, CW | | | MED | | | | |
|---|---|---|---|---|---|---|---|
| ADDITIVE: | Amount, g | # | 0 | 5 | 10 | 15 | 20 |
| Octocrylene (Positive Control) | 5 | 1 | 380 | 377 | 377 | 377 | 377 |
| Pentylene Glycol | 5 | 2 | 381 | 378 | 376 | 369 | 355 |
| Etoxydiglycol | 5 | 3 | 379 | 378 | 373 | 369 | 367 |
| BG Monopropionate | 5 | 4 | 378 | 376 | 373 | 365 | 363 |

TABLE 8-continued

Critical Wavelength

| Critical Wavelength, CW | | | | | | | |
|---|---|---|---|---|---|---|---|
| | | | | MED | | | |
| ADDITIVE: | Amount, g | # | 0 | 5 | 10 | 15 | 20 |
| 1,2-Octanediol | 5 | 5 | 382 | 381 | 379 | 378 | 376 |
| Isopropyl Myristate (Negative Control) | 5 | 6 | 378 | 375 | 370 | 355 | 350 |
| 1,2-Hexanediol + 1,2-Octanediol | 5 | 7 | 379 | 376 | 370 | 358 | 348 |
| Diethylene Glycol Monobutyl Ether | 5 | 8 | 379 | 377 | 373 | 364 | 357 |
| 1,2-Hexanediol | 5 | 9 | 378 | 375 | 367 | 356 | 349 |
| Octocrylene + 1,2-Octanediol | 2.5 + 2.5 | 10 | 381 | 380 | 380 | 379 | 379 |
| No additives (Negative Control) | 0 | 11 | 380 | 377 | 370 | 364 | 362 |
| PEG-7 Methyl Ether | 5 | 12 | 380 | 377 | 370 | 361 | 351 |
| Octocrylene (Positive Control) | 2.5 | 13 | 381 | 378 | 378 | 377 | 376 |
| octocrylene and PEG-7 Methyl Ether | 2.5 + 2.5 | 14 | 380 | 378 | 378 | 378 | 378 |
| Octocrylene + 1,2-Octanediol + PEG-7 Methyl Ether | 2.5 + 1.25 + 1.25 | 15 | 381 | 380 | 379 | 379 | 379 |

Figure 2:
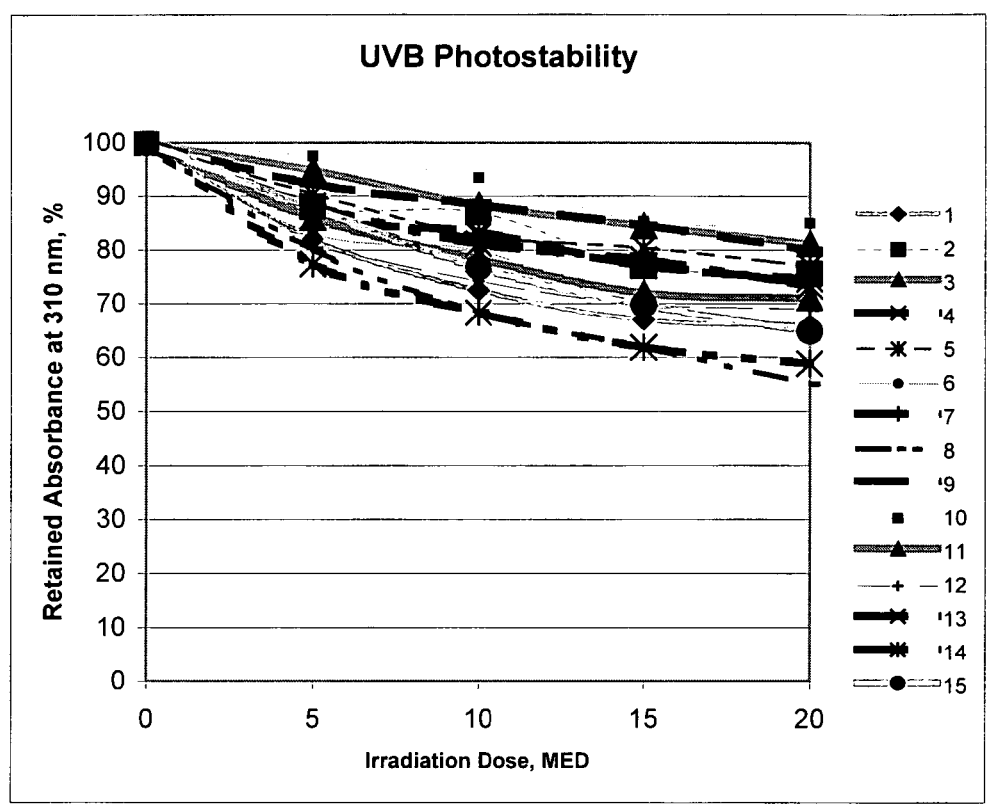
FIG. 2 is a graph depicting the UVB photostability of compositions according to the present invention and comparative examples.
Figure 3:
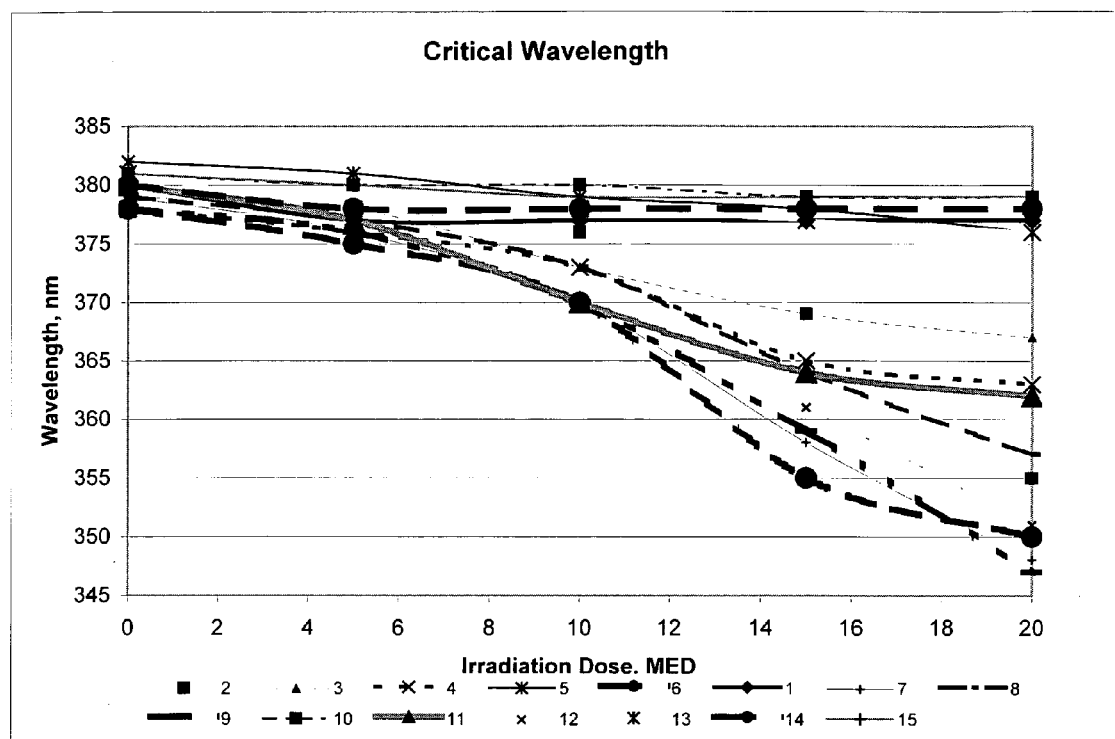
FIG. 3 is a graph depicting the critical wavelength of compositions according to the present invention and comparative examples.

As is evident by the results outlined in the graphs of FIGS. 1 and 2, as well as Table 8 and the graph of FIG. 3, it was unexpectedly found that the polarity of an oil phase alone is not just a single factor that affects the photostability of UVA sunscreens, such as avobenzone and its derivatives. Glycol or glycol derivative structure may also play a very important role in photostability. For example, sunscreen compositions containing 1,2-octanediol, BG monopropionate and 1,2-hexanediol have very similar dielectric constants (8.0–8.1). However, only 1,2-octanediol most effectively stabilizes avobenzone. It stabilizes avobenzone by increasing the retained absorbance at 370 nm, 310 nm, and minimizing the decrease of Critical Wavelength (CW) after UV irradiation.

It was also found unexpectedly that certain glycols, for example, pentylene glycol, ethoxydiglycol, BG monopropionate and 1,2-hexanediol can improve the photostability of UVB sunscreens at 310 nm without the significant improvement of the photostability of avobenzone at 370 nm and also critical wavelength.

Mechanisms of photostabilizing UVA and UVB sunscreens by diols, glycols and their derivatives may include, but are not limited to, external stabilization by hydrogen bonding. In addition, the one or more optimization agents, such as, for example, caprylyl glycol and pentylene glycol (most preferred optimizing agents) do not have σ-π bonds and unsaturated groups in their molecular structures. In addition, most preferred optimizing agents (caprylyl glycol and pentylene glycol) are 1,2-diols.

EXAMPLE 4

Referring to Table 2 above, the PFA of MF2822-1 and MF2822-2 compositions was measured by JCIA Method (methods described in co-pending patent application Ser. No. 10/779,314, filed Feb. 13, 2004, which is incorporated in its entirety by reference herein). PFA value is an indicator of a sunscreen's protection in UVA region, which is associated with photoaging, as opposed to the UVB region, which is associated with sunburn. PFA is also is related to the degree of photostabilization of UVA sunscreens, such as avobenzone and its derivatives. So a PFA boost to a sunscreen composition will directly correlate with higher UVA efficacy of a sunscreen as well as a higher degree of photostabilization of a UVA sunscreen.

It has been unexpectedly found that the inclusion of one or more optimization agents in a photoprotective composition according to the present invention results in a PFA boost to the composition, as compared to a composition without one or more optimization agents. A PFA boost on the order on at least 10% is experienced by the compositions according to the present invention. Particularly, a PFA boost on the order of greater than about 50% is experienced, and more particularly a PFA boost of greater than about 85% is experienced by a composition according to the present invention, as compared to a composition without one or more optimization agents.

PFA values for MF2822-1 and MF 2822-2 are outlined in Table 9 below.

TABLE 9

| Average PFA Values | |
|---|---|
| MF2822-1 | MF2822-2 |
| 10.34 | 5.51 |

The results of PFA tests have shown that the addition of 5 wt. % of 1,2-octanediol to the sunscreen formulation provided a PFA (PPD, JCIA) boost by almost 5 PFA units (about 88%) when compared to the formulation without 1,2-octanediol.

In addition to the above-described unexpected features of the present invention, it has also unexpectedly been found that there exists a synergistic effect on the photostability of UVA sunscreen, such as avobenzone and its derivatives, when octocrylene and one or more optimization agents, such as 1,2-octanediol (caprylyl glycol) are both present in a sunscreen composition. As a result of this synergistic effect, a photoprotective composition according to the present invention possesses at least a 10% increase in UVA photostability, at least a 10% increase in UVB photostability and a decrease in critical wavelength, as compared to a composition without the synergistic combination according to the present invention.

The one or more optimization agents to octocrylene may be present in a photoprotective composition in a weight ratio of about 0.01 to about 100. Preferably, the synergistic combination is present in a ratio between about 0.1 to about 10, and more preferably about 0.5 to about 5.

EXAMPLE 5

Referring to Table 10 below, octocrylene and/or 1,2-octanediol were added to the following sunscreen components: AVOBENZONE—3 g; HOMOSALATE—15 g; OCTYL SALICYLATE—5 g; which are intended to resemble an oil phase of a sunscreen composition. It is noted that the base composition #'s 1, 5, 10 and 11 are described in Table 2 above.

TABLE 10

| ADDITIVE: | Compositions g | Table 2 Comp. |
|---|---|---|
| Octocrylene (Positive Control) | 5 | 1 |
| 1,2-Octanediol | 5 | 5 |
| Octocrylene + 1,2-Octanediol | 2.5 + 2.5 | 10 |
| No additives (Negative Control) | 0 | 11 |

The above compositions were applied on Vitro-Skin (0.6 mg/cm2) and irradiated. The irradiation dose was 5 MEDs repeated 4 times (=20 MEDs total). Retained Absorbance at 370 nm (Table 11 and FIG. 4), 310 nm (Table 12) and critical wavelength (Table 13 and FIG. 5) were determined for each composition before and after each irradiation dose in order to determine their photostability. The methodology is described above in more detail in Example 3.

TABLE 11

UVA Photostability

UVA Photostability 370 nm

| ADDITIVE: | Amount, g | # | 0 | 5 | MED 10 | 15 | 20 |
|---|---|---|---|---|---|---|---|
| Octocrylene (Positive Control) | 5 | 1 | 100 | 75 | 66 | 63 | 61 |
| 1,2-Octanediol | 5 | 5 | 100 | 89.9 | 72.9 | 58.9 | 45.1 |
| Octocrylene + 1,2-Octanediol | 2.5 + 2.5 | 10 | 100 | 83 | 74 | 65 | 64 |
| No additives (Negative Control) | 0 | 11 | 100 | 64 | 29 | 16 | 12 |

TABLE 12

UVB Photostability

UVB Photostability, 310 nm

| ADDITIVE: | Amount, g | # | 0 | 5 | MED 10 | 15 | 20 |
|---|---|---|---|---|---|---|---|
| Octocrylene (Positive Control) | 5 | 1 | 100 | 82 | 72.5 | 67 | 66 |
| 1,2-Octanediol | 5 | 5 | 100 | 90.4 | 82.8 | 80.4 | 77.1 |
| Octocrylene + 1,2-Octanediol | 2.5 + 2.5 | 10 | 100 | 97.4 | 93.4 | 85.3 | 85 |
| No additives (Negative Control) | 0 | 11 | 100 | 86 | 78.3 | 72 | 71 |

TABLE 13

Critical Wavelength

Critical Wavelength, CW

| ADDITIVE: | Amount, g | # | 0 | 5 | MED 10 | 15 | 20 |
|---|---|---|---|---|---|---|---|
| Octocrylene (Positive Control) | 5 | 1 | 380 | 377 | 377 | 377 | 377 |
| 1,2-Octanediol | 5 | 5 | 382 | 381 | 379 | 378 | 376 |
| Octocrylene + 1,2-Octanediol | 2.5 + 2.5 | 10 | 381 | 380 | 380 | 379 | 379 |

TABLE 13-continued

Critical Wavelength

Critical Wavelength, CW

| ADDITIVE: | Amount, g | # | 0 | 5 | MED 10 | 15 | 20 |
|---|---|---|---|---|---|---|---|
| 1,2-Octanediol No additives (Negative Control) | 0 | 11 | 380 | 377 | 370 | 364 | 362 |

Figure 4:
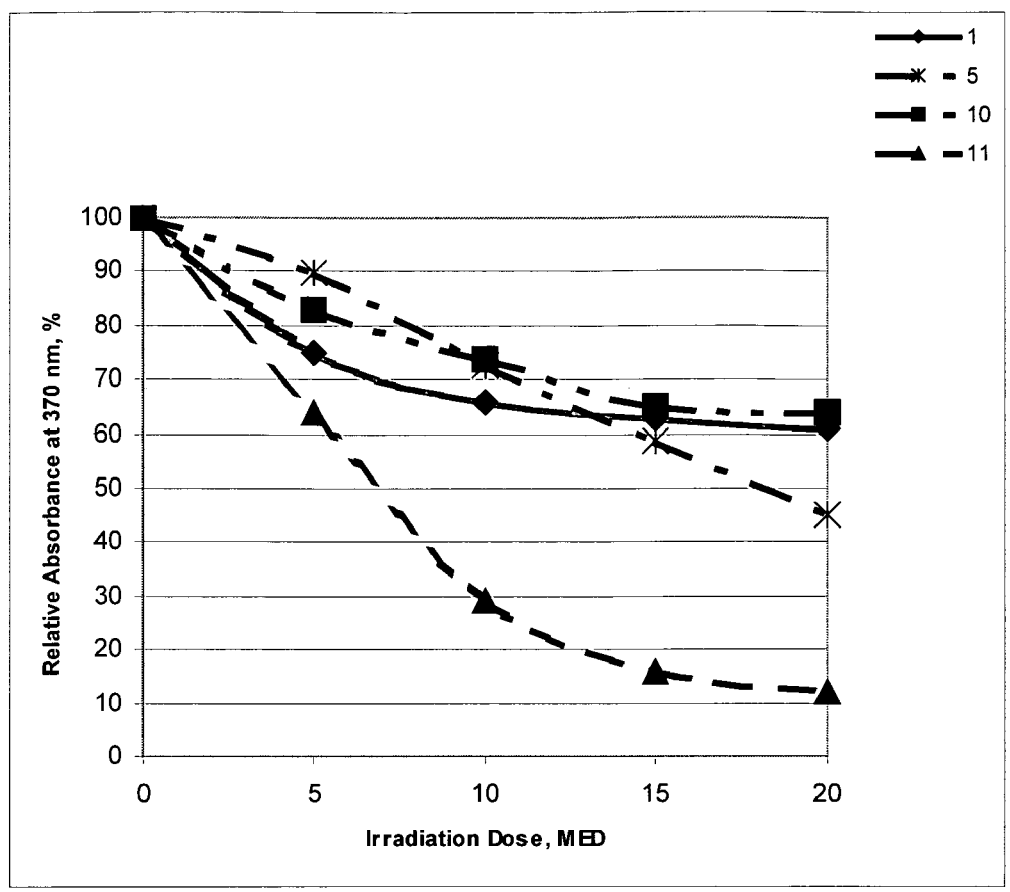
FIG. 4 is a graph depicting the UVA photostability of compositions with a synergistic combination of optimizing agent and octocrylene according to the present invention.
Figure 5:
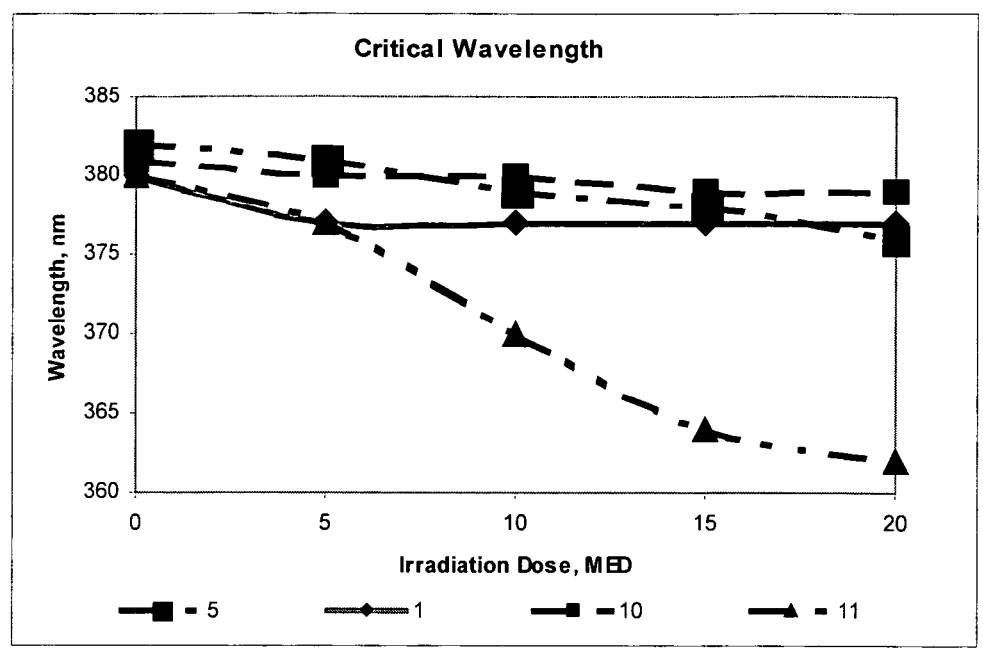
FIG. 5 is a graph depicting the critical wavelength of compositions with a synergistic combination of optimizing agent and octocrylene according to the present invention.

As is evident from the above tables, in conjunction with graphs set forth in FIGS. 4 and 5, the composition with 2.5 g octocrylene and 2.5 g of 1,2 octanediol, provides better photostabilization of avobenzone than 5 g of octocrylene alone. Therefore, there is an unexpected synergistic effect on the photostabilization of avobenzone by using both octocrylene and 1,2 octanediol. Surprisingly, the UVB photostabilization is also achieved by the synergistic effect of the combination of octocrylene and 1,2 octanediol.

In addition, unexpectedly, the critical wavelength of the composition including the synergistic combination of octocrylene and 1,2 octanediol has been stabilized.

In another embodiment of the present invention, it has been surprisingly found that certain molar ratios of the one or more optimization agents according to the present invention to one or more dibenzoylmethane derivatives, such as avobenzone, results in a highly photostable composition.

Suitable molar ratio ranges for dibenzoylmethane derivative, according to the present invention are between about 0.016M to about 0.193M. Preferably, the molar range is between about 0.048M to about 0.096M. The dibenzoylmethane derivative is present in the composition in an amount about 0.5 wt. % to about 6 wt. %.

Suitable molar ratios for the one or more optimization agents to dibenzoylmethane derivative is between about 0.5 to about 400. Preferable, the molar ratio of one or more optimization agent to dibenzoylmethane derivative is about 0.5 to about 100 and more preferably about 0.5 to 10.

This embodiment of the present invention is demonstrated below in Example 6, with avobenzone as the dibenzoylmethane derivative.

EXAMPLE 6

In order to determine the impact of the concentration of avobenzone, from 0.04842 M to 0.0968 M (Factor 1) and different molar ratios of 1,2-octanediol (caprylyl glycol) to avobenzone, from 0 to 10 (Factor 2), on the photostability of avobenzone in the different sunscreen compositions, numerous studies were conducted. Three designs of experiments that represent central composite designs (CCDs) and D.O.E. Fusion 7.2.2 software were employed.

Experimental Set-Up

The CCD type of design was used to determine the effect of two factors: concentration of Avobenzone and the molar ratio 1,2-octanediol/avobenzone on the photostability of avobenzone in the different sunscreen compositions. Two responses were measured: the retained absorbance (%) of a sunscreen composition at 370 nm (UVA) and the same measurement at 310 nm (UVB) after irradiation dose of 15 MED.

TABLE 14

Ranges for the Two Experimental Factors

| Factor | Range |
|---|---|
| Avobenzone Concentration | 0.04842M to 0.0968M |
| Glycol/Avo Molar Ratio | 0 to 10 |

Table 15 below presents the experimental CCD set-up used. The second column presents the experimental order in which the experiments were carried out, since order randomization is necessary

TABLE 15

Experimental CCD

| Std | Run | Factor 1 A:Avobenzone M | Factor 2 B:Molar Ratio Glycol:Avo |
|---|---|---|---|
| 1 | 8 | 0.055505 | 1.4645 |
| 2 | 10 | 0.089715 | 1.4645 |
| 3 | 7 | 0.055505 | 8.5355 |
| 4 | 12 | 0.089715 | 8.5355 |
| 5 | 1 | 0.04842 | 5 |
| 6 | 13 | 0.0968 | 5 |
| 7 | 6 | 0.07261 | 0 |
| 8 | 11 | 0.07261 | 10 |
| 9 | 3 | 0.07261 | 5 |
| 10 | 9 | 0.07261 | 5 |
| 11 | 4 | 0.07261 | 5 |
| 12 | 2 | 0.07261 | 5 |
| 13 | 5 | 0.07261 | 5 |

The same order of experiments was run in the different set-ups. As a result, two categorical factors were added: Oxybenzone (absent or present at a predetermined constant level) and Octocrylene (absent or present at a predetermined constant level). Table 16 presents the three set-ups as well as the numbers of the formulation tables and response tables.

TABLE 16

Full Experimental Runs

| | Avobenzone and Glycol/Avo CCD | Oxybenzone | Octocrylene | Formulation Table | Results Table |
|---|---|---|---|---|---|
| DOE 1 | Yes | Absent | Absent | Table 17 | Table 18 |
| DOE 2 | Yes | Present | Absent | Table 19 | Table 20 |
| DOE 3 | Yes | Present | Present | Table 21 | Table 22 |

Response surface equalization were fitted to both responses (retained absorbance at 370 nm and retained absorbance at 310 nm, both after an irradiation dose of 15 MED). The significant factors were selected.

Response 1: Retained Absorbance at 370 nm after Irradiation at 15 MED

Figure 6:
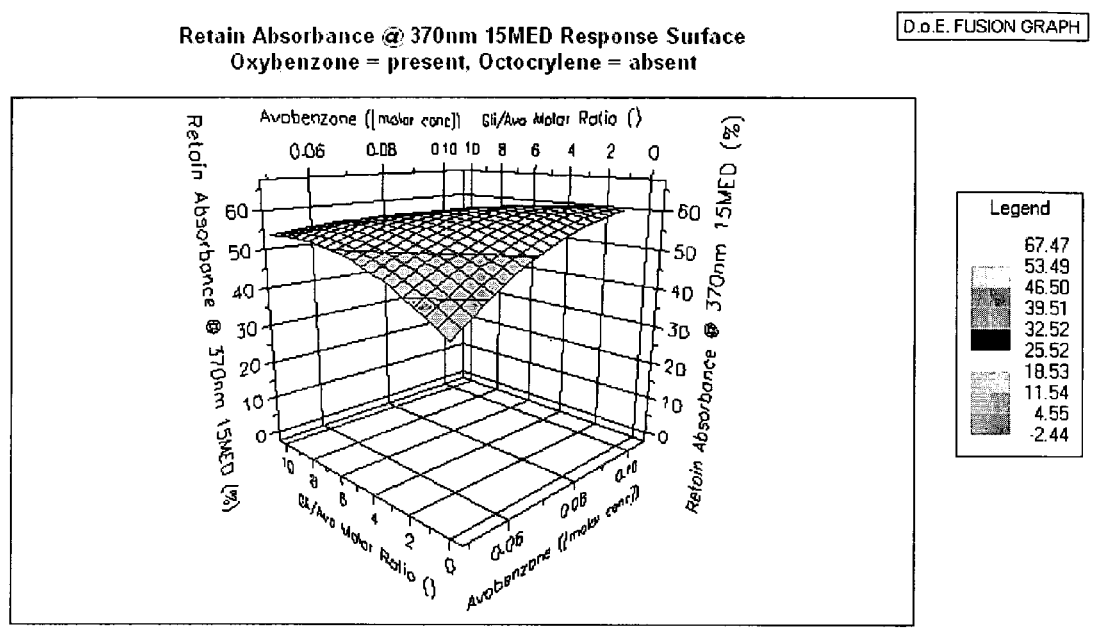
FIG. 6 is a fusion graph depicting the photostability of avobenzone in a photoprotective composition according to the present invention.

The response surface model indicates a high fit ($R^2=0.9534$). The presence of Oxybenzone in the system (model oil phase) gives the highest boost in retain absorbance at 370 nm and 15 MED exposure, as demonstrated by the graph in FIG. 6. An interaction between the presence of oxybenzone and the level of the glycol/avobenzone ratio was observed. This may suggest that at a high level of glycol/avobenzone oxybenzone may interact with the glycol and affect the stability of avobenzone.

There is a significant effect of the glycol/avobenzone ratio. This effect shows a statistically significant improvement in the measured response and it is stronger for lower concentration of avobenzone.

Figure 7:
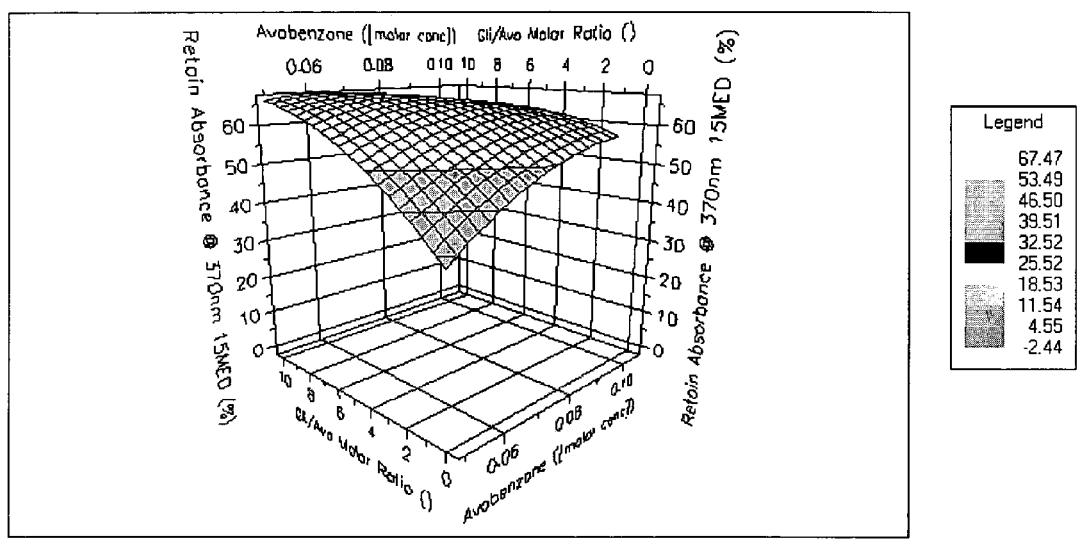
FIG. 7 is another fusion graph depicting the photostability of avobenzone in a photoprotective composition according to the present invention.

Higher concentrations of avobenzone help a better retention. The presence of octocrylene helps the absorbance retention 370 nm, but not as significant as in the case of oxybenzone. This effect seems to be enhanced at higher level glycol/avobenzone ratios. The graph of FIG. 7 demonstrates these results.

Response 2: Retain Absorbance at 310 nm after Irradiation at 15 MED

The response surface model indicates a moderate fit ($R^2=0.6668$). Oxybenzone helps retention at 310 nm where a mild jump in response especially at the lower levels of glycol/avobenzone ratio. Octocrylene also gives mild a gain in absorbency especially at higher levels of glycol/avobenzone and low levels of avobenzone. The higher concentration of avobenzone has a positive impact on the response, especially in the presence of octocrylene.

TABLE 17

DOE 1 Formulations

| | | | | | | RUN #: | | | | | | | | |
|---|---|---|---|---|---|---|---|---|---|---|---|---|---|---|
| DOE 1 | 1 | 2 | 3 | 4 | 5 | 6 | 7 | 8 | 9 | 10 | 11 | 12 | 13 |
| MODEL OF OIL PHASE: | | | | | | | | | | | | | |
| Homosalate | 11 | 11 | 11 | 11 | 11 | 11 | 11 | 11 | 11 | 11 | 11 | 11 | 11 |
| Octyl Salicylate | 5 | 5 | 5 | 5 | 5 | 5 | 5 | 5 | 5 | 5 | 5 | 5 | 5 |
| Avobenzone | 1.5 | 2.3 | 2.3 | 2.3 | 2.3 | 2.3 | 1.7 | 1.7 | 2.3 | 2.8 | 2.3 | 2.8 | 3 |
| 1,2-Octanediol | 3.5 | 5.3 | 5.3 | 5.3 | 5.3 | 0 | 6.9 | 1.2 | 5.3 | 1.9 | 10.6 | 11 | 7 |

TABLE 17-continued

DOE 1 Formulations

| DOE 1 | RUN #: | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Neopentyl Glycol Diheptanoate QS to 30 g | 9 | 6.4 | 6.4 | 6.4 | 6.4 | 11.7 | 5.4 | 11.1 | 6.4 | 9.3 | 1.1 | 0 | 4 |
| | 30 | 30 | 30 | 30 | 30 | 30 | 30 | 30 | 30 | 30 | 30 | 30 | 30 |

TABLE 18

UVA and UVB Photostabilization for DOE 1

| DOE 1 Run | Factor 1 A:Avo, M | Factor 2 B:Molar Ratio Octanediol:Avo | Dielectric Constant 23 C. | Retained Abs, % at 370 nm after 15 MED | Retained Abs, % at 310 nm after 15 MED |
|---|---|---|---|---|---|
| 1 | 0.04842 | 5 | 6.1 | 20 | 65 |
| 2 | 0.07261 | 5 | 6.64 | 25 | 73 |
| 3 | 0.07261 | 5 | 6.64 | 30 | 76 |
| 4 | 0.07261 | 5 | 6.64 | 29 | 79 |
| 5 | 0.07261 | 5 | 6.64 | 26 | 77 |
| 6 | 0.07261 | 0 | 5.58 | 13 | 61 |
| 7 | 0.055505 | 8.5355 | 6.78 | 26 | 67 |
| 8 | 0.055505 | 1.4645 | 5.69 | 17 | 62 |
| 9 | 0.07261 | 5 | 6.64 | 27 | 74 |
| 10 | 0.089715 | 1.4645 | 6.11 | 17 | 66 |
| 11 | 0.07261 | 10 | 7.8 | 33 | 77 |
| 12 | 0.089715 | 8.5355 | 8.08 | 24 | 72 |
| 13 | 0.0968 | 5 | 7.24 | 31 | 76 |

TABLE 19

DOE 2

| DOE 2 | RUN #: | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| MODEL OF OIL PHASE: | | | | | | | | | | | | | |
| Homosalate | 11 | 11 | 11 | 11 | 11 | 11 | 11 | 11 | 11 | 11 | 11 | 11 | 11 |
| Octyl Salicylate | 5 | 5 | 5 | 5 | 5 | 5 | 5 | 5 | 5 | 5 | 5 | 5 | 5 |
| Oxybenzone | 6 | 6 | 6 | 6 | 6 | 6 | 6 | 6 | 6 | 6 | 6 | 6 | 6 |
| Avobenzone | 1.5 | 2.3 | 2.3 | 2.3 | 2.3 | 2.3 | 1.7 | 1.7 | 2.3 | 2.8 | 2.3 | 2.8 | 3 |
| 1,2-Octanediol | 3.5 | 5.3 | 5.3 | 5.3 | 5.3 | 0 | 6.9 | 1.2 | 5.3 | 1.9 | 10.6 | 11 | 7 |
| Neopentyl Glycol Diheptanoate QS to 36 g | 9 | 6.4 | 6.4 | 6.4 | 6.4 | 11.7 | 5.4 | 11.1 | 6.4 | 9.3 | 1.1 | 0 | 4 |
| | 36 | 36 | 36 | 36 | 36 | 36 | 36 | 36 | 36 | 36 | 36 | 36 | 36 |

TABLE 20

UVA and UVB Photostabilization for DOE 2

| DOE 2 Run | Factor 1 A:Avo, M | Factor 2 B:Molar Ratio Octanediol:Avo | Dielectric Constant 23 C. | Retained Abs, % at 370 after 15 MED | Retained Abs, % at 370 after 15 MED |
|---|---|---|---|---|---|
| 1 | 0.04842 | 5 | 7.2 | 47 | 70 |
| 2 | 0.07261 | 5 | 7.7 | 62 | 81 |
| 3 | 0.07261 | 5 | 7.7 | 60 | 79 |
| 4 | 0.07261 | 5 | 7.7 | 62 | 80 |
| 5 | 0.07261 | 5 | 7.7 | 62 | 81 |
| 6 | 0.07261 | 0 | 6.7 | 44 | 63 |
| 7 | 0.055505 | 8.5355 | 7.9 | 56 | 75 |
| 8 | 0.055505 | 1.4645 | 6.7 | 51 | 74 |
| 9 | 0.07261 | 5 | 7.7 | 61 | 79 |
| 10 | 0.089715 | 1.4645 | 7.2 | 61 | 79 |
| 11 | 0.07261 | 10 | 8.7 | 58 | 78 |

TABLE 20-continued

UVA and UVB Photostabilization for DOE 2

| DOE 2 Run | Factor 1 A:Avo, M | Factor 2 B:Molar Ratio Octanediol:Avo | Dielectic Constant 23 C. | Retained Abs, % at 370 after 15 MED | Retained Abs, % at 370 after 15 MED |
|---|---|---|---|---|---|
| 12 | 0.089715 | 8.5355 | 8.9 | 51 | 66 |
| 13 | 0.0968 | 5 | 8.1 | 63 | 85 |

TABLE 21

DOE 3

| DOE 3 | RUN #: 1 | 2 | 3 | 4 | 5 | 6 | 7 | 8 | 9 | 10 | 11 | 12 | 13 |
|---|---|---|---|---|---|---|---|---|---|---|---|---|---|
| MODEL OF OIL PHASE: | | | | | | | | | | | | | |
| Homosalate | 11 | 11 | 11 | 11 | 11 | 11 | 11 | 11 | 11 | 11 | 11 | 11 | 11 |
| Octyl Salicylate | 5 | 5 | 5 | 5 | 5 | 5 | 5 | 5 | 5 | 5 | 5 | 5 | 5 |
| Oxybenzone | 6 | 6 | 6 | 6 | 6 | 6 | 6 | 6 | 6 | 6 | 6 | 6 | 6 |
| Octocrylene | 2.5 | 2.5 | 2.5 | 2.5 | 2.5 | 2.5 | 2.5 | 2.5 | 2.5 | 2.5 | 2.5 | 2.5 | 2.5 |
| Avobenzone | 1.5 | 2.3 | 2.3 | 2.3 | 2.3 | 2.3 | 1.7 | 1.7 | 2.3 | 2.8 | 2.3 | 2.8 | 3 |
| 1,2-Octanediol | 3.5 | 5.3 | 5.3 | 5.3 | 5.3 | 0 | 6.9 | 1.2 | 5.3 | 1.9 | 10.6 | 11 | 7 |
| Neopentyl Glycol Diheptanoate QS to 38.5 g | 9 | 6.4 | 6.4 | 6.4 | 6.4 | 11.7 | 5.4 | 11.1 | 6.4 | 9.3 | 1.1 | 0 | 4 |
| | 38.5 | 38.5 | 38.5 | 38.5 | 38.5 | 38.5 | 38.5 | 38.5 | 38.5 | 38.5 | 38.5 | 38.5 | 38.5 |

TABLE 22

UVA and UVB Photostabilization for DOE 3

| DOE 3 Run | Factor 1 A:Avo, M | Factor 2 B:Molar Ratio Octanediol:Avo | Dielectic Constant 23 C. | Retained Abs, % at 370 nm after 15 MED | Retained Abs, % at 310 nm after 15 MED |
|---|---|---|---|---|---|
| 1 | 0.04842 | 5 | 7.40 | 54 | 78 |
| 2 | 0.07261 | 5 | 8.10 | 61 | 85 |
| 3 | 0.07261 | 5 | 8.10 | 63 | 79 |
| 4 | 0.07261 | 5 | 8.10 | 63 | 81 |
| 5 | 0.07261 | 5 | 8.10 | 63 | 81 |
| 6 | 0.07261 | 0 | 7.10 | 60 | 72 |
| 7 | 0.055505 | 8.5355 | 8.10 | 77 | 97 |
| 8 | 0.055505 | 1.4645 | 7.10 | 47 | 72 |
| 9 | 0.07261 | 5 | 8.10 | 63 | 81 |
| 10 | 0.089715 | 1.4645 | 7.40 | 60 | 70 |
| 11 | 0.07261 | 10 | 8.90 | 63 | 81 |
| 12 | 0.089715 | 8.5355 | 9.20 | 66 | 82 |
| 13 | 0.0968 | 5 | 8.50 | 62 | 75 |

The overall analysis of the results of DOE 1, 2 and 3 shows that 1,2-octanediol (caprylyl glycol) significantly improves the photostability of sunscreens at 310 nm (UVB sunscreens) and at 370 nm (UVA sunscreens such as Avobenzone). The concentration of avobenzone, molar ratio of 1,2-octanediol (caprylyl glycol) to avobenzone and also other sunscreens that are present in the sunscreen composition significantly influence the degree of photostabilization at 310 nm and 370 nm provided by 1,2-octanediol.

It should be understood that while many of the embodiments of the present invention were exemplified above through the testing and analysis of oil phases of a photoprotective composition, the unexpected results are even more enhanced in final photoprotective compositions (versus just an oil phase alone), due in part to the inclusion of additional components, such as those described below.

Additional Components

The one or more optimization agents are preferably included in a solvent system used to dissolve the one or more photoactive compounds. As used herein, a solvent system includes all of the compounds used to dissolve the one or more photoactive compounds. By way of example, the solvent system for cosmetic sunscreen compositions will include lipophilic compounds for dissolving oil miscible photoactive compounds and hydrophilic compounds for dissolving water miscible photoactive compounds. In a preferred embodiment, the solvent system includes one or more optimization agents that are both oil miscible and water miscible. Such agents offer a distinct advantage when formulating the sunscreen composition, as the need for separate oil and water miscible solvents is reduced or eliminated.

In addition to the one or more optimization agents, the solvent system may include, but is not limited to, one or more solvents, such as $C_{12}$–$C_{15}$ alkyl benzoates, capric triglycerides, caprylic triglycerides, diethylhexyl adipate, diethylhexyl malate, diethylhexyl 2,6-naphthalate, ethylhexyl palmitate, ethylhexyl stearate, isoeicosane, isopropyl myristate, isopropyl palmitate, mineral oil, octyldodecyl neopentanoate, polyisobutene, PPG-2 myristyl ether propionate, cocoglycerides, isostearyl linoleate, diisopropyl adipate, myristyl ether myristate, octyl palmitate, propylene glycol ricinoleate, cetyl esters, propylene glycol laurate, or any combinations thereof. Although not necessary, it is preferred that the one or more solvents, when used with photoactive compounds such as those identified above, have a dielectric constant of about 1 to about 12. By using highly polar solvents, in addition to dissolving the one or more photoactive compounds, the solvents may contribute to the overall polarity of the composition.

In addition to the one or more photoactive compounds and the one or more optimizing agents, any well-known cosmetically-acceptable additives, such as, for example, water, emulsifier, thickening agent, emollient, SPF booster, moisturizer, humectant, film former/waterproofing agent, bioactive (functional) ingredient, pH adjuster/chelating agent, preservative, fragrance, effect pigment, color additive, lubricant, elastomer, or any combinations thereof, and/or other common cosmetic formulation additives for solubility of sunscreen active compounds, emulsification, thickening and to provide other skin enhancement, e.g., moisturizing properties, may be included in the sunscreen composition.

The compositions of the present invention preferably include water. The water is present in the compositions of the present invention in an amount about 40 wt. % to about 90 wt. %, and preferably about 50 wt. % to about 80 wt. %, of the total weight of the compositions.

The compositions of the present invention may include one or more emulsifiers. The one or more emulsifiers suitable for use in the present invention include, but are not limited to, acrylates crosspolymer, acrylates/$C_{10\text{-}30}$ alkylacrylate crosspolymer, acrylates/vinyl isodecanoate crosspolymer, polyacrylic acid, sodium polymethacrylate, sodium polyacrylate, polyacrylates, cetyl alcohol, cetearyl alcohol, oleth-10, diethylhexyl esters, sorbitan oleate, sorbitan sesquioleate, sorbitan isostearate, sorbitan trioleate, PEG-20 almond glycerides, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, sodium glyceryl oleate phosphate, hydrogenated vegetable glycerides phosphate, or any combinations thereof.

The amount of emulsifier present in the compositions of the present invention is about 0.01 wt. % to about 10 wt. % of the total weight of the composition. Preferably, the emulsifier is present in an amount about 0.1 wt. % to about 5 wt. % of the total weight of the composition.

In an alternative embodiment, the sunscreen composition of the present invention may be formulated to be emulsifier free, which can improve water resistance of the sunscreen formulation and reduce its irritation potential.

One or more thickening agents that may be used in the compositions of the present invention. Suitable thickening agent includes, but is not limited to, one or more stabilizers, synthetic and natural gum or polymer products, polysaccharide thickening agents, associative thickeners, anionic associative rheology modifiers, nonionic associative rheology modifiers, oil-thickening agents, acrylates/C10–30 alkyl acrylate crosspolymer, acrylates/aminoacrylates/C10–30 alkyl PEG-20 itaconate copolymer, acrylates copolymer, acrylates/steareth-20 methacrylate copolymer, acrylates/beheneth-25 methacrylate copolymer, PEG-150/decyl alcohol/SMDI copolymer, PVP, PVM/MA decadiene crosspolymer, carbomer, PEG crosspolymer, acrylates/palmeth-25 acrylates copolymer, polysaccharides, polyacrylates, polyether-1, sodium magnesium silicate, sodium carbomer, sodium polyacrylate, sodium polymethacrylate, sodium polyacryloyldimethyl taurate, sodium acryloyldimethyl taurate copolymer, sodium carragenan, sodium carboxymethyl dextran, hydroxyethylcellulose, hydroxypropyl cyclodextran, bentonites, trihydroxystearin, aluminum-magnesium hydroxide stearate, xanthan gum, or any combinations thereof.

The amount of thickening agent present in the compositions of the present invention is about 0.01 wt. % to about 10 wt. % of the total weight of the composition. Preferably, the thickener is present in an amount about 0.1 wt. % to about 5 wt. % of the total weight of the composition.

The present compositions may include one or more emollients. An emollient provides a softening, protective or soothing effect on the skin surface and is generally considered safe for topical use. It also helps control the rate of evaporation and the tackiness of the compositions.

Suitable emollients include, for example, cocoglycerides, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid such as oleic and stearic, fatty alcohol such as cetyl and hexadecyl, diisopropyl adipate, hydroxybenzoate esters, benzoic acid esters of $C_9$–$C_{15}$ alcohols, isononyl isononanoate, alkanes such as mineral oil, silicone such as dimethyl polysiloxane, ether such as polyoxypropylene butyl ether and polyoxypropylene cetyl ether, $C_{12}$–$C_{15}$ alkyl benzoate, or any combinations thereof.

The total amount of emollient present in the compositions is typically about 0.1 wt. % to about 30 wt. % of the total weight of the composition. Preferably, emollient is present in an amount about 1 wt. % to about 20 wt. % of the total weight of the composition.

The pH of the compositions of the present invention may be adjusted by one or more basic pH adjusters and/or chelating agents. For example, sodium hydroxide, triethanolamine, EDTA salts, or any combinations thereof are suitable pH adjusters/chelating agents that may be included in the sunscreen compositions of the present invention.

An effective amount of a pH adjuster and/or chelating agent is included to adjust the pH of the final compositions to about 3 to about 9. Preferably, the pH is adjusted to about 5 to about 8 and more preferably about 6 to about 7.

One or more humectants may be used in the compositions of the present invention. Suitable humectants include, but are not limited to, glycerin, pentylene glycol, hexylene glycol, propylene glycol, butylene glycol, sorbitol, PEG-4, or any combinations thereof.

One or more humectants may be included in the compositions of the present invention in an amount about 0.1 wt. % to about 15 wt. % of the total weight of the composition. Preferably, humectant is present in an amount about 1 wt. % to about 5 wt. % of the total weight of the composition. The present compositions may include one or more SPF boosters. SPF booster itself is not an active ingredient, but is designed to enhance the effectiveness of the sunscreen actives present in the formulation. Suitable SPF boosters include, but are not limited to, styrene/acrylates copolymer, sodium bentonites, highly purified white sodium bentonites, montmorillonite, hydrogels, fluorene derivatives, ester derivatives of cyano(9H-fluoren-9-ylidene), amides, malates, bis-urethanes, or any combinations thereof. A preferred styrene/acrylates copolymer for use in the present invention is sold under the trade name SunSpheres® by Rohm and Haas Company.

When present, the one or more SPF boosters may be included in the compositions of the present invention in an amount about 1 wt. % to about 6 wt. % of the total weight of the composition. Preferably, SPF booster is present in an amount about 2 wt. % to about 3 wt. % of the total weight of the composition.

Another component that may be used in the compositions of the present invention is a film former/waterproofing agent. The film former/waterproofing agent is a hydrophobic material that imparts film forming and waterproofing characteristics to the emulsion. Suitable film former/waterproofing agent for use in the compositions of the present invention include, but is not limited to, acrylates/acrylamide copolymer, acrylates copolymer, acrylates/$C_{12-22}$ alkylmethacrylate copolymer, polyethylene, waxes, VP/Dimethiconylacrylate/Polycarbamyl polyglycol ester, butylated PVP, PVP/Hexadecene copolymer, octadecene/MA copolymer, PVP/Eicosene copolymer, tricontanyl PVP, Brassica Campestris/Aleuritis Fordi Oil copolymer, decamethyl cyclopentasiloxane (and) trimethylsiloxysilicate, or any combinations thereof.

One or more film formers/waterproofing agents may be present in the compositions of the present invention in an amount about 0.1 wt. % to about 5 wt. % of the total weight of the composition. Preferably, the one or more film formers/waterproofing agents is present in the compositions of the present invention in an amount about 1 wt. % to about 3 wt. % of the total weight of the composition.

In addition, it has been unexpectedly found that the acrylates/$C_{12-22}$ alkylmethacrylate copolymer may protect the lipids in a user's skin by imparting structure to the epidermal lipids in the skin (stratum corneum) and sebaceous lipids (sebum) and preventing them from depletion. As a result, it is believed that the acrylates/$C_{12-22}$ alkylmethacrylate copolymer may enhance and help to maintain the barrier properties of the lipid barrier in stratum corneum.

Therefore, the compositions of the present invention may exhibit moisturizing and anti-inflammatory properties without a need for including moisturizers and/or anti-inflammatory agents in the compositions.

One or more preservatives may be included in the compositions of the present invention. The preservative protects the compositions from microbial contamination and/or oxidation. As such, the preservative can include an antioxidant. Preservatives, such as diazolidinyl urea, iodopropynyl butylcarbamate, chloromethylisotiazolinone, methylisothiazolinone, vitamin E and its derivatives including vitamin E acetate, vitamin C, butylated hydroxytoluene, butylparaben, ethylparaben, methylparaben, propylparaben, isobutylparaben, phenoxyethanol, or any mixtures thereof, may be included as a preservative in a composition of the present invention.

About 0.01 wt. % to about 2 wt. % of preservative may be included in a composition of the present invention. Preferably, one or more preservatives total about 0.5 wt. % to about 1.5 wt. % of the total weight of the composition.

The compositions of the present invention may also have other optional additives including bio-active (functional) ingredients. For instance, one or more plant extracts, fruit extracts, vegetable extracts, algae extracts, sugars, polysaccharides, lipids, proteins, peptides, aminoacids, aminoacid derivatives, absorbents, elastomers, for example DC 9011 silicone elastomer blend (Dow Corning) (cyclopentasiloxane (and) PEG-12 (and) dimethicone crosspolymer), salicylic acid, alpha and beta hydroxy acids, oil and water soluble vitamins including vitamins A, C, and E and their derivatives, or any mixtures thereof, may be included in the sunscreen compositions.

When present, the optional additives may be included in the present composition in an amount about 0.001 wt. % to about 10 wt. %, based on the total weight of the composition.

The compositions can be produced as lotions, creams, ointments, gels, solid sticks, emulsions, aerosols, solutions, dispersions, or any other forms of cosmetic compositions.

Further aspects of the invention may become apparent to those skilled in the art from a review of the detailed description set forth above. It should be understood that the disclosure is merely illustrative, and is not intended to limit the invention to the specific embodiments described.

We claim:

1. A photoprotective composition comprising:
   one or more sunscreen agents; and
   one or more optimizing agents selected from the group consisting of diol, alcohol, glycol, polyhydric alcohol, any derivatives thereof, and any combinations thereof, wherein said photoprotective composition has one or more optimized properties selected from the group consisting of polarity, critical wavelength, SPF, PFA, Star Rating, photostability, and any combinations thereof, as compared to a composition without said one or more optimizing agents.

2. The photoprotective composition of claim 1, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyl-dibenzoylmethane, metal oxides, titanium dioxide, zinc oxide, and any combinations thereof.

3. The photoprotective composition of claim 1, wherein said one or more sunscreen agents are present in an amount about 1 wt. % to about 40 wt. %, based on the total weight of the composition.

4. The photoprotective composition of claim 1, wherein said one or more optimizing agents are one or more diols, glycols, and any combinations thereof.

5. The photoprotective composition of claim 1, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

6. The photoprotective composition of claim 1, wherein said one or more optimizing agents are one or more glycols selected from the group consisting of 1,2-pentanediol, 1,2-octanediol, and any combination thereof.

7. The photoprotective composition of claim 1, wherein said one or more optimizing agents is present in said composition in an amount about 0.1 wt. % to about 40 wt. %, based on the total weight of the composition.

8. The photoprotective composition of claim 1, wherein said one or more optimizing agents is present in said composition in an amount about 0.1 wt. % to about 10 wt. %, based on the total weight of the composition.

9. The photoprotective composition of claim 1, wherein said one or more optimizing agents, taken alone or in combination, has a dielectric constant greater than about 10.5.

10. The photoprotective composition of claim 1, wherein said one or more optimizing agents, taken alone or in combination, has a dielectric constant greater than about 13.

11. The photoprotective composition of claim 1, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

12. A photoprotective composition comprising:
one or more sunscreen agents; and
one or more optimizing agents selected from the group consisting of diol, alcohol, glycol, polyhydric alcohol, any derivatives thereof, and any combinations thereof, wherein said one or more optimizing agents, taken alone or in combination, has a dielectric constant greater than about 13.

13. The photoprotective composition of claim 12, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyl-dibenzoylmethane, metal oxides, titanium dioxide, zinc oxide, and any combinations thereof.

14. The photoprotective composition of claim 12, wherein said one or more sunscreen agents are present in an amount about 1 wt. % to about 40 wt. %, based on the total weight of the composition.

15. The photoprotective composition of claim 12, wherein said one or more optimizing agents are one or more glycols selected from the group consisting of pentylene glycol, neopentyl glycol, caprylyl glycol, 1,2-octanediol, etoxydiglycol, butylene glycol monopropionate, diethylene glycol monobutyl ether, PEG-7 methyl ether, octacosanyl glycol, arachidyl glycol, benzyl glycol, cetyl glycol, $C_{14-18}$ glycol, $C_{15-18}$ glycol, lauryl glycol, butoxydiglycol, 1,10-decanediol, ethyl hexanediol, and any combinations thereof.

16. The photoprotective composition of claim 12, wherein said one or more optimizing agents are one or more glycols selected from the group consisting of 1,2-pentanediol, 1,2-octanediol, and any combination thereof.

17. The photoprotective composition of claim 12, wherein said one or more optimizing agents is present in said composition in an amount about 0.1 wt. % to about 40 wt. %, based on the total weight of the composition.

18. The photoprotective composition of claim 12, wherein said one or more optimizing agents is present in said composition in an amount about 0.1 wt. % to about 10 wt. %, based on the total weight of the composition.

19. The photoprotective composition of claim 12, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

20. A photoprotective composition comprising:
one or more sunscreen agents; and
one or more optimizing agents selected from the group consisting of diol, alcohol, glycol, polyhydric alcohol, any derivatives thereof, and any combinations thereof, wherein said one or more optimizing agents increase a SPF of said composition by at least 25% compared to a composition without said one or more optimizing agents.

21. The photoprotective composition of claim 20, wherein said one or more optimizing agents increase a SPF of said composition by at least about 30% compared to a composition without said one or more optimizing agents.

22. The photoprotective composition of claim 20, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyl-dibenzoylmethane, metal oxides, titanium dioxide, zinc oxide, and any combinations thereof.

23. The photoprotective composition of claim 20, wherein said one or more sunscreen agents are present in an amount about 1 wt. % to about 40 wt. %, based on the total weight of the composition.

24. The photoprotective composition of claim 20, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

25. The photoprotective composition of claim 20, wherein said one or more optimizing agents are one or more glycols selected from the group consisting of 1,2-pentanediol, 1,2-octanediol, and any combination thereof.

26. The photoprotective composition of claim 20, wherein said one or more optimizing agents is present in said composition in an amount about 0.1 wt. % to about 40 wt. %, based on the total weight of the composition.

27. The photoprotective composition of claim 20, wherein said one or more optimizing agents is present in said composition in an amount about 0.1 wt. % to about 10 wt. %, based on the total weight of the composition.

28. The photoprotective composition of claim 20, wherein said one or more optimizing agents, taken alone or in combination, has a dielectric constant greater than about 10.5.

29. The photoprotective composition of claim 20, wherein said one or more optimizing agents, taken alone or in combination, has a dielectric constant greater than about 13.

30. The photoprotective composition of claim 20, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

31. A photoprotective composition comprising:
one or more sunscreen agents; and
one or more optimizing agents selected from the group consisting of diol, alcohol, glycol, polyhydric alcohol, any derivatives thereof, and any combinations thereof,
wherein said one or more optimizing agents increase a PFA of said composition by at least 10% compared to a composition without said one or more optimizing agents.

32. The photoprotective composition of claim 31, wherein said one or more optimizing agents increase a PFA of said composition by at least about 85% compared to a composition without said one or more optimizing agents.

33. The photoprotective composition of claim 31, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyl-dibenzoylmethane, metal oxides, titanium dioxide, zinc oxide, and any combinations thereof.

34. The photoprotective composition of claim 31, wherein said one or more sunscreen agents are present in an amount about 1 wt. % to about 40 wt. %, based on the total weight of the composition.

35. The photoprotective composition of claim 31, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

36. The photoprotective composition of claim 31, wherein said one or more optimizing agents are one or more glycols selected from the group consisting of 1,2-pentanediolpentylene glycol, 1,2-octanediol, and any combination thereof.

37. The photoprotective composition of claim 31, wherein said one or more optimizing agents is present in said composition in an amount about 0.1 wt. % to about 40 wt. %, based on the total weight of the composition.

38. The photoprotective composition of claim 31, wherein said one or more optimizing agents is present in said composition in an amount about 0.1 wt. % to about 10 wt. %, based on the total weight of the composition.

39. The photoprotective composition of claim 31, wherein said one or more optimizing agents, taken alone or in combination, has a dielectric constant greater than about 10.5.

40. The photoprotective composition of claim 31, wherein said one or more optimizing agents, taken alone or in combination, has a dielectric constant greater than about 13.

41. The photoprotective composition of claim 31, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

42. A photoprotective composition comprising:
a synergistic combination of octocrylene and one or more optimizing agents selected from the group consisting of diol, alcohol, glycol, polyhydric alcohol, any derivatives thereof, and any combinations thereof,
wherein, as a result of said synergistic combination, said photoprotective composition has an increase in a UVA photostability of at least about 10%, an increase in a UVB photostability of at least about 10% and a decrease in a critical wavelength as compared to a composition without said synergistic combination of octocrylene and one or more optimizing agents.

43. The photoprotective composition of claim 42, wherein said synergistic combination of one or more optimizing agents and octocrylene is present in a weight ratio of one or more optimizing agents to octocrylene of about 0.1 to about 10.

44. The photoprotective composition of claim 42, further comprising one or more sunscreen agents selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, 4-isopropyldibenzoylmethane, metal oxides, titanium dioxide, zinc oxide, and any combinations thereof.

45. The photoprotective composition of claim 44, wherein said one or more sunscreen agents are present in an amount about 1 wt. % to about 40 wt. %, based on the total weight of the composition.

46. The photoprotective composition of claim 42, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

47. The photoprotective composition of claim 42, wherein said one or more optimizing agents are one or more glycols selected from the group consisting of 1,2-pentanediol, 1,2-octanediol, and any combination thereof.

48. The photoprotective composition of claim 42, wherein said one or more optimizing agents is present in said composition in an amount about 0.1 wt. % to about 40 wt. %, based on the total weight of the composition.

49. The photoprotective composition of claim 42, wherein said one or more optimizing agents is present in said composition in an amount about 0.1 wt. % to about 10 wt. %, based on the total weight of the composition.

50. The photoprotective composition of claim 42, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

51. A photoprotective composition comprising:
one or more dibenzoylmethane derivatives;
one or more additional sunscreen agents; and
one or more optimizing agents selected from the group consisting of diol, alcohol, glycol, polyhydric alcohol, any derivatives thereof, and any combinations thereof,
wherein said one or more dibenzoylmethane derivatives is present in a molar concentration between about 0.016 M to about 0.193 M, and
wherein said one or more optimizing agents to said one or more dibenzoylmethane derivatives are present in said composition in a molar ratio of about 0.5 to about 400.

52. The photoprotective composition of claim 51, wherein said one or more dibenzoylmethane derivatives is present in a molar concentration between about 0.048 M to about 0.096 M.

53. The photoprotective composition of claim 51, wherein said one or more optimizing agents to said one or more dibenzoylmethane derivatives are present in said composition in a molar ratio of about 0.5 to about 10.

54. The photoprotective composition of claim 51, wherein said one or more dibenzoylmethane derivatives is selected from the group consisting of avobenzone, 4-isopropyldibenzoylmethane, butylmethoxydibenzoylmethane, 4-isopropyl-dibenzoylmethane, and any combinations thereof.

55. The photoprotective composition of claim 51, wherein said one or more additional sunscreen agents are selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, octocrylene, metal oxides, titanium dioxide, zinc oxide, and any combinations thereof.

56. The photoprotective composition of claim 51, wherein said one or more dibenzoylmethane derivatives are present in an amount about 0.5 wt. % to about 6 wt. %, based on the total weight of the composition.

57. The photoprotective composition of claim 51, wherein said one or more additional sunscreen agents are present in an amount about 1 wt. % to about 40 wt. %, based on the total weight of the composition.

58. The photoprotective composition of claim 51, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

59. The photoprotective composition of claim 51, wherein said one or more optimizing agents are one or more glycols selected from the group consisting of 1,2-pentanediol, 1,2-octanediol, and any combination thereof.

60. The photoprotective composition of claim 51, wherein said one or more optimizing agents is present in said composition in an amount about 0.1 wt. % to about 40 wt. %, based on the total weight of the composition.

61. The photoprotective composition of claim 51, wherein said one or more optimizing agents is present in said composition in an amount about 0.1 wt. % to about 10 wt. %, based on the total weight of the composition.

62. The photoprotective composition of claim 51, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

63. A photoprotective composition comprising:
one or more sunscreen agents; and
one or more optimizing agents selected from the group consisting of 1,2-octanediol, 1,2-pentanediol, and combinations thereof,
wherein said one or more optimizing agents optimizes one or more properties selected from the group consisting of polarity, critical wavelength, SPF, PFA, Star Rating, photostability, and any combinations thereof, of said composition, as compared to a composition without said one or more optimizing agents.

64. The photoprotective composition of claim 63, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyl-dibenzoylmethane, metal oxides, titanium dioxide, zinc oxide, and any combinations thereof.

65. The photoprotective composition of claim 63, wherein said one or more sunscreen agents are present in an amount about 1 wt. % to about 40 wt. %, based on the total weight of the composition.

66. The photoprotective composition of claim 63, wherein said one or more optimizing agents is present in said composition in an amount about 0.1 wt. % to about 40 wt. %, based on the total weight of the composition.

67. The photoprotective composition of claim 63, wherein said one or more optimizing agents is present in said composition in an amount about 0.1 wt. % to about 10 wt. %, based on the total weight of the composition.

68. The photoprotective composition of claim 63, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

69. A method of providing an efficient photoprotective composition comprising the steps of:
formulating a photoprotective composition with one or more sunscreen agents and one or more optimizing agents selected from the group consisting of diol, alcohol, glycol, polyhydric alcohol, any derivatives thereof, and any combinations thereof,
wherein said photoprotective composition has one or more optimized properties selected from the group consisting of polarity, critical wavelength, SPF, PFA, Star Rating, photostability, and any combinations thereof, as compared to a composition without said one or more optimizing agents.

70. The method of claim 69, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyl-dibenzoylmethane, metal oxides, titanium dioxide, zinc oxide, and any combinations thereof.

71. The method of claim 69, wherein said one or more sunscreen agents are present in an amount about 1 wt. % to about 40 wt. %, based on the total weight of the composition.

72. The method of claim 69, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

73. The method of claim 69, wherein said one or more optimizing agents are one or more glycols selected from the group consisting of pentylene glycol, 1,2-octanediol, and any combination thereof.

74. The method of claim 69, wherein said one or more optimizing agents is present in said composition in an amount about 0.1 wt. % to about 40 wt. %, based on the total weight of the composition.

75. The method of claim 69, wherein said one or more optimizing agents is present in said composition in an amount about 0.1 wt. % to about 10 wt. %, based on the total weight of the composition.

76. The method of claim 69, wherein said one or more optimizing agents, taken alone or in combination, has a dielectric constant greater than about 10.5.

77. The method of claim 69, wherein said one or more optimizing agents, taken alone or in combination, has a dielectric constant greater than about 13.

78. The method of claim 69, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

79. A method for optimizing a polarity, critical wavelength, SPF, PFA, Star Rating, photostability, or any combinations thereof, in a photoprotective composition comprising the step of:
formulating said photoprotective composition with one or more sunscreen agents and one or more optimizing agents selected from the group consisting of diol, alcohol, glycol, polyhydric alcohol, any derivatives thereof, and any combinations thereof,
wherein said photoprotective composition has one or more optimized properties selected from the group consisting of polarity, critical wavelength, SPF, PFA, Star Rating, photostability, and any combinations thereof, as compared to a composition without said one or more optimizing agents.

80. The method of claim 79, wherein said one or more sunscreen agents is selected from the group consisting of p-aminobenzoic acid, p-aminobenzoic acid salts, p-aminobenzoic acid derivatives, anthranilates, salicylates, glyceryl ester, dipropyleneglycol esters, cinnamic acid derivatives, dihydroxycinnamic acid derivatives, camphor, camphor derivatives, trihydroxycinnamic acid derivatives, hydrocarbons, dibenzalacetone, benzalacetophenone, naptholsulfonates, dihydroxy-naphthoic acid, dihydroxy-naphthoic acid salts; o-hydroxydiphenyldisulfonates, p-hydroxydiphenyldisulfonates, coumarin derivatives, diazoles, quinine salts, quinoline derivatives, hydroxy-substituted benzophenones, methoxy-substituted benzophenones, uric acids, vilouric acids, tannic acid, tannic acid derivatives, hydroquinone, benzophenones, avobenzone, 4-isopropyldibenzoylmethane, butylmethoxydibenzoylmethane, octocrylene, 4-isopropyldibenzoylmethane, metal oxides, titanium dioxide, zinc oxide, and any combinations thereof.

81. The method of claim 79, wherein said one or more sunscreen agents are present in an amount about 1 wt. % to about 40 wt. %, based on the total weight of the composition.

82. The method of claim 79, wherein said one or more optimizing agents are one or more glycols selected from the group consisting of pentylene glycol (1,2-pentanediol), neopentyl glycol (neopentanediol), caprylyl glycol (1,2-octanediol), ethoxydiglycol, butylene glycol monopropionate, diethylene glycol monobutyl ether, PEG-7 methyl ether, octacosanyl glycol, arachidyl glycol, benzyl glycol, cetyl glycol (1,2-hexanediol), $C_{14-18}$ glycol, $C_{15-18}$ glycol, lauryl glycol (1,2-dodecanediol), butoxydiglycol, 1,10-decanediol, ethyl hexanediol, or any combinations thereof.

83. The method of claim 79, wherein said one or more optimizing agents are one or more glycols selected from the group consisting of 1,2-pentanediol, pentylene glycol, 1,2-octanediol, and any combination thereof.

84. The method of claim 79, wherein said one or more optimizing agents is present in said composition in an amount about 0.1 wt. % to about 40 wt. %, based on the total weight of the composition.

85. The method of claim 79, wherein said one or more optimizing agents is present in said composition in an amount about 0.1 wt. % to about 10 wt. %, based on the total weight of the composition.

86. The method of claim 79, wherein said one or more optimizing agents, taken alone or in combination, has a dielectric constant greater than about 10.5.

87. The method of claim 79, wherein said one or more optimizing agents, taken alone or in combination, has a dielectric constant greater than about 13.

88. The method of claim 79, wherein said composition further comprises one or more components selected from the group consisting of solvent, water, emulsifier, thickening agent, emollient, SPF booster, moisturizer, humectant, film former/waterproofing agent, bio-active, pH adjuster/chelating agent, preservative, fragrance, effect pigment, color additive, lubricant, elastomer, and any combinations thereof.

89. The photoprotective composition according to claim 1, further comprising an oil-phase, wherein said one or more optimizing agents are in said oil-phase.

90. The photoprotective composition according to claim 12, further comprising an oil-phase, wherein said one or more optimizing agents are in said oil-phase.

91. The photoprotective composition according to claim 20, further comprising an oil-phase, wherein said one or more optimizing agents are in said oil-phase.

92. The photoprotective composition according to claim 63, further comprising an oil-phase, wherein said one or more optimizing agents are in said oil-phase.

93. The photoprotective composition according to claim 69, further comprising an oil-phase, wherein said one or more optimizing agents are in said oil-phase.

94. The photoprotective composition according to claim 79, further comprising an oil-phase, wherein said one or more optimizing agents are in said oil-phase.

* * * * *